(12) United States Patent
Heller et al.

(10) Patent No.: US 9,976,133 B2
(45) Date of Patent: May 22, 2018

(54) SYNZYMES

(71) Applicant: The Regents of the University of California, La Jolla, CA (US)

(72) Inventors: Michael J. Heller, Poway, CA (US); Tsukasa Takahashi, San Diego, CA (US); Michelle Lillian Cheung, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 12 days.

(21) Appl. No.: 14/406,999

(22) PCT Filed: Jun. 20, 2013

(86) PCT No.: PCT/US2013/046845
§ 371 (c)(1),
(2) Date: Dec. 10, 2014

(87) PCT Pub. No.: WO2013/192430
PCT Pub. Date: Dec. 27, 2013

(65) Prior Publication Data
US 2015/0175993 A1    Jun. 25, 2015

Related U.S. Application Data

(60) Provisional application No. 61/662,302, filed on Jun. 20, 2012.

(51) Int. Cl.
| | |
|---|---|
| *C12N 9/50* | (2006.01) |
| *C07K 7/06* | (2006.01) |
| *C07K 7/08* | (2006.01) |
| *C12N 13/00* | (2006.01) |

(52) U.S. Cl.
CPC .................. *C12N 9/50* (2013.01); *C07K 7/06* (2013.01); *C07K 7/08* (2013.01); *C12N 13/00* (2013.01); *C12Y 304/22* (2013.01); *G01N 2333/95* (2013.01)

(58) Field of Classification Search
None
See application file for complete search history.

(56) References Cited

U.S. PATENT DOCUMENTS

| | | | | |
|---|---|---|---|---|
| 5,503,989 A * | 4/1996 | Bibbs | .................... | C07K 14/575 |
| 6,048,690 A | 4/2000 | Heller et al. | | |
| 2004/0077037 A1* | 4/2004 | Bordusa | .................... | C07K 7/06 435/68.1 |
| 2007/0055453 A1 | 3/2007 | Heller | | |
| 2011/0131679 A2 | 6/2011 | La Rosa et al. | | |
| 2011/0251372 A1* | 10/2011 | Sommen | ............... | C07K 5/1016 530/326 |
| 2011/0318380 A1* | 12/2011 | Brix | .................... | A61K 39/0011 424/193.1 |
| 2013/0330335 A1* | 12/2013 | Bremel | ................... | G06F 19/18 424/134.1 |

FOREIGN PATENT DOCUMENTS

| | | |
|---|---|---|
| DE | 19617202 | 11/1997 |
| DE | 19953696 | 5/2001 |
| WO | WO 1999/040433 | 8/1999 |
| WO | WO 2003/099862 | 12/2003 |
| WO | WO 2010/037395 | 4/2010 |
| WO | WO201037395 A2 * | 8/2010 |
| WO | WO 2010/139736 | 12/2010 |

OTHER PUBLICATIONS

Coyle and Young. (Protection of Cysteine and Histidine by the Diphenyl-4-pyridylmethyl Group during Peptide Synthesis, J.C.S. Chem. Comm., 1976, 980-981).*
Joseph et al. Draft Genome Sequence of the Halophilic and Highly Halotolerant Gammaproteobacteria Strain MFB021, Nov./Dec. 2014 vol. 2 Issue 6 e01156-14.*
International Search Report and Written Opinion in International Application No. PCT/US2013/046845, dated Nov. 28, 2013, 9 pages.
International Preliminary Report on Patentability in International Application No. PCT/US2013/046845, dated Dec. 31, 2014, 7 pages.
Carrea, et al., "Polyamino acids as synthetic enzymes: mechanism, applications and relevance to prebiotic catalysis," Trends Biotechnol., 23(10):507-13 (Oct. 2005).
Heller et al., "Intramolecular catalysis of acylation and deacylation in peptides containing cysteine and histidine," JACS, 99(8):2780-2785 (Apr. 13, 1977).
Kisailus et al., "Self-assembled bifunctional surface mimics an enzymatic and templating protein for the synthesis of a metal oxide semiconductor," PNAS USA, 103(15):5652-5657 (Apr. 11, 2006).
Roberge et al., "A strategy for a convergent synthesis of N-linked glycopeptides on a solid support," Science, 269:202-204 (Jul. 14, 1995).
Roth et al., "Bifunctional small molecules are biomimetic catalysts for silica synthesis at neutral pH," JACS, 127:325-330 (Jan. 12, 2005).
Walder et al., "Complementary carrier peptide synthesis: general strategy and implications for prebiotic origin of peptide synthesis," PNAS USA, 76(1):51-55 (Jan. 1979).
European Search Report in European Application No. 13806372.2, dated Apr. 20, 2017, 6 pages.
Heller et al., "Peptide nanoparticle catalysis," Nanotech Conference & Expo 2012: An Interdisciplinary Integrative Forum on Nanotechnology, Microtechnology, Biotechnology, and Cleantechnology, Santa Clara, CA, United States, Jun. 18-21, 2012(1): 499-501 Abstract.
Sahu et al., "Peptides that inhibit factors B and C2 and Complement Activation, and their uses," Mar. 16, 2012, XP002752208, Retrieved from STN Database Accession No. 2012:443584, 1 page, Abstract.
Supplemental European Search Report in European Application No. 13806372.2, dated Jan. 22, 2016, 6 pages.

* cited by examiner

*Primary Examiner* — Jeanette M Lieb
(74) *Attorney, Agent, or Firm* — Fish & Richardson P.C.

(57) ABSTRACT

Novel synthetic catalytic structures or "synzymes," e.g., synthetic polypeptides, with catalytic properties are provided. It is believed that these synthetic catalytic structures mimic some of the precise conformational changes necessary for catalytic activities seen in enzymes. The catalytic properties of these synthetic catalytic structures or synzymes can be further improved by the application of controlled external forces, e.g., electric fields.

31 Claims, 12 Drawing Sheets

(SEQ ID NO: 33)

(SEQ ID NO: 36)

ously favors the reverse reaction for  reforming the acyl-sulfhydryl/thiol group.

SEQUENCE LISTING

```
<160> NUMBER OF SEQ ID NOS: 40

<210> SEQ ID NO 1
<211> LENGTH: 5
<212> TYPE: PRT
<213> ORGANISM: Artificial Sequence
<220> FEATURE:
<223> OTHER INFORMATION: synthetic polypeptide
<220> FEATURE:
<221> NAME/KEY: VARIANT
```

```
<222> LOCATION: 1, 3, 5
<223> OTHER INFORMATION: Xaa = alanine, an alanine analog, phenylalanine
      and a phenylalanine analog
<220> FEATURE:
<221> NAME/KEY: VARIANT
<222> LOCATION: 2, 4
<223> OTHER INFORMATION: Xaa = cysteine, a cysteine analog, serine, a
      serine analog, histidine, and a histidine analog

<400> SEQUENCE: 1

Xaa Xaa Xaa Xaa Xaa
1               5

<210> SEQ ID NO 2
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 2

Ala Cys Ala His Ala
1               5

<210> SEQ ID NO 3
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 3

Ala Ser Ala His Ala
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 4

Phe Cys Phe His Ala
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 5

Phe Ser Phe His Ala
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 6

Phe His Phe Cys Ala
1               5
```

```
<210> SEQ ID NO 7
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 7

Phe His Phe Ser Ala
1               5

<210> SEQ ID NO 8
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 8

Ala Cys Ala His Ala Asp
1               5

<210> SEQ ID NO 9
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 9

Ala Ser Ala His Ala Asp
1               5

<210> SEQ ID NO 10
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 10

Phe Cys Phe His Ala Asp
1               5

<210> SEQ ID NO 11
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 11

Phe Ser Phe His Ala Asp
1               5

<210> SEQ ID NO 12
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 12

Asp Phe His Phe Cys Ala
1               5
```

```
<210> SEQ ID NO 13
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 13

Asp Phe His Phe Ser Ala
1               5

<210> SEQ ID NO 14
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 14

Ala Ala Cys Ala His Ala Asp
1               5

<210> SEQ ID NO 15
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 15

Ala Ala Ser Ala His Ala Asp
1               5

<210> SEQ ID NO 16
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 16

Ala Phe Cys Phe His Ala Asp
1               5

<210> SEQ ID NO 17
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 17

Ala Phe Ser Phe His Ala Asp
1               5

<210> SEQ ID NO 18
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 18

Asp Phe His Phe Cys Ala Gly
1               5

<210> SEQ ID NO 19
```

```
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 19

Asp Phe His Phe Ser Ala Gly
1               5

<210> SEQ ID NO 20
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 20

Gly Ala Ala Cys Ala His Ala Asp
1               5

<210> SEQ ID NO 21
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 21

Gly Ala Ala Ser Ala His Ala Asp
1               5

<210> SEQ ID NO 22
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 22

Gly Ala Phe Cys Phe His Ala Asp
1               5

<210> SEQ ID NO 23
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 23

Gly Ala Phe Ser Phe His Ala Asp
1               5

<210> SEQ ID NO 24
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 24

Asp Phe His Phe Cys Ala Gly Asp
1               5

<210> SEQ ID NO 25
<211> LENGTH: 8
```

```
<212> TYPE: PRT
<213> ORGANISM: Artificial Sequence
<220> FEATURE:
<223> OTHER INFORMATION: synthetic polypeptide

<400> SEQUENCE: 25

Asp Phe His Phe Ser Ala Gly Asp
 1               5

<210> SEQ ID NO 26
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 26

Gly Gly Ala Ala Cys Ala His Ala Asp
 1               5

<210> SEQ ID NO 27
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 27

Arg Gly Ala Ala Cys Ala His Ala Asp
 1               5

<210> SEQ ID NO 28
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 28

Arg Gly Ala Ala Ser Ala His Ala Asp
 1               5

<210> SEQ ID NO 29
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 29

Arg Gly Ala Phe Cys Phe His Ala Asp
 1               5

<210> SEQ ID NO 30
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 30

Lys Gly Ala Phe Cys Phe His Ala Asp
 1               5

<210> SEQ ID NO 31
<211> LENGTH: 9
<212> TYPE: PRT
```

<213> ORGANISM: Artificial Sequence
<220> FEATURE:
<223> OTHER INFORMATION: synthetic polypeptide

<400> SEQUENCE: 31

Arg Gly Ala Phe Ser Phe His Ala Asp
1               5

<210> SEQ ID NO 32
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 32

Lys Gly Ala Phe Ser Phe His Ala Asp
1               5

<210> SEQ ID NO 33
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 33

Arg Asp Phe His Phe Cys Ala Gly Asp
1               5

<210> SEQ ID NO 34
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 34

Arg Asp Phe His Phe Ser Ala Gly Asp
1               5

<210> SEQ ID NO 35
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 35

His Gly Gly Pro Gly Gly His Gly Cys Gly Asp
1               5                   10

<210> SEQ ID NO 36
<211> LENGTH: 13
<212> TYPE: PRT
<213> ORGANISM: Artificial Sequence
<220> FEATURE:
<223> OTHER INFORMATION: synthetic polypeptide

<400> SEQUENCE: 36

Arg Gly His Gly Gly Pro Gly Gly His Gly Cys Gly Asp
1               5                   10

<210> SEQ ID NO 37
<211> LENGTH: 14
<212> TYPE: PRT
<213> ORGANISM: Artificial Sequence

```
<220> FEATURE:
<223> OTHER INFORMATION: synthetic polypeptide

<400> SEQUENCE: 37

Arg Gly Gly His Phe Cys Gly Pro Gly His Gly His Gly Asp
 1               5                  10

<210> SEQ ID NO 38
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 38

Gly Gly Ala Ala Cys Ala Ser Ala Asp
 1               5

<210> SEQ ID NO 39
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 39

Arg Gly Ala Ala Cys Ala Ser Ala Asp
 1               5

<210> SEQ ID NO 40
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 40

Arg Asp Phe Asn Phe Cys Ala Gly Asp
 1               5
```

SYNZYMES

CROSS-REFERENCE TO RELATED APPLICATIONS

This application is a National Stage application under 35 U.S.C. § 371 of International Application No. PCT/US2013/046845, having an International Filing Date of Jun. 20, 2013, which claims priority to and the benefit of U.S. Provisional Application No. 61/662,302, which was filed on Jun. 20, 2012, and is incorporated by reference in its entirety.

TECHNICAL FIELD

The present invention relates to synthetic polypeptides and other synthetic catalytic structures ("synzymes") with catalytic properties, and the methods, devices, and systems that are utilized together with such synthetic catalytic structures.

BACKGROUND

Of all the macromolecules in living organisms, enzymes represent those which are the most complex in terms of structure and mechanistic properties. Enzymes are able to catalyze the transformation of all other biomolecules, providing the dynamics and very essence of life. Enzymes can aptly be considered natural bionanomachines which do chemistry. In particular, enzymes are proteins that accelerate the chemical transformation of a substrate molecule that binds to the active site of the enzyme in a thermodynamically and mechanically favorable manner, resulting in a chemical transformation of the substrate into a product molecule. Such enzyme catalyzed chemical transformations can include hydrolysis, oxidation/reduction, group transfer, isomerization, addition or removal of groups from double bonds, and ligation reactions. Enzymes catalyze reactions with high specificity and enormous rate accelerations, some having turnover numbers of millions of substrate molecules per second.

In the case of certain proteases, a catalytic triad is thought to be primarily responsible for the efficient hydrolysis (cleavage) of amide bonds in proteins and polypeptides, as well as ester bonds in certain biomolecule and synthetic substrates. For a serine protease such as Chymotrypsin, the catalytic triad motif is a close proximity arrangement of the serine ("Ser") 195, the histidine ("His") 57 and the aspartate ("Asp") 102 amino acid residues in the polypeptide chain. In this catalytic triad, the serine hydroxyl group acts as a strong nucleophile, the histidine imidazole group as a general acid/base and the aspartate carboxyl group helps orient the histidine imidazole group and neutralize the charge that develops during the transition states. With the aid of this hydrogen bonding and exchange network within the reaction site, the catalytic triad functions as a reversible charge relay mechanism where protons are thought to be exchanged from one residue to another producing an efficient catalytic mechanism. While the stereochemical fit and binding between the substrate and enzyme is very important, it is the complex three dimensional ("3D") protein structure which actually produces the dynamic mechanical properties in the catalytic triad that lead to efficient enzyme catalysis and turnover.

Most scientists who study enzymology are well aware that the remarkable catalytic properties of enzymes come from their complex 3D protein structure. Upon binding a substrate molecule, the enzyme carries out a rapid set of precise chemo-mechanical dynamic movements which converts the substrate(s) into the product molecule(s).

Over the past three decades a number of efforts have been made to create synthetic versions of enzymes which are sometimes called synzymes or enzyme mimics. Many of the synzymes are based on peptides, synthetic macromolecules and more recently nanostructures that are designed to closely resemble the active site of an enzyme. While these synthetic structures look similar to the enzyme active site they may not have the unique mechanical or dynamic catalytic properties to transform a substrate molecule into the desired product molecule in a repeated process i.e., turnover. Early work by one of the inventors of the present invention involved synthetic peptide structures which contain the same basic catalytic groups, a cysteine-sulfhydryl/thiol, a histidine-imidazole and an aspartate-carboxyl, that are in found the active site of Papain (Heller M J, Walder J A and Klotz I M, JACS, 99(8): 2780-2785, 1977). The synthetic peptide structures of that study were found not to exhibit any efficient catalytic properties, particularly with regard to turnover.

The natural enzyme Papain is a cysteine protease from the papaya plant, whose active site catalytic triad (Cys 25, His 159, and Asp 158) efficiently catalyzes the hydrolysis (cleavage) of both peptide (amide) bonds and ester bonds. Papain has a catalytic mechanism similar to Chymotypsin; the only difference is that a cysteine sulfhydryl/thiol group is the primary nucleophile in Papain. In Papain catalysis, the cysteine sulfhydryl/thiol group carries out a nucleophilic attack on the substrate amide/ester bond forming an acyl-cysteine intermediate. The histidine imidazole group is involved in the deacylation of the acyl-cysteine intermediate which leads to rapid turnover of the enzyme. In the case of the synthetic peptide structures which mimicked the Papain active site, acyl-group exchange was observed between the acyl-cysteine and the imidazole group however, back-attack by the cysteine sulfhydryl/thiol group prevented catalysis and any turnover in these synthetic peptide mimics. In this particular case, the back-attack is more formally an example of an intra-molecular acyl-transfer reaction between the cysteine sulfhydryl/thiol and the histidine imidazole, where the equilibrium greatly favors the reverse reaction for reforming the acyl-sulfhydryl/thiol group.

Other early work by one of the inventors of the present invention involved using synthetic DNA structures to catalyze the formation of peptide bonds (Walder et al., PNAS USA, 76 (1):51-55, 1979). This work demonstrated the potential for using amino acid modified DNA/RNA hybridizing structures and DNA templates to catalyze amide bond formation for peptide synthesis reactions. While the hybridized DNA/RNA structures provided very close proximity for the reacting groups, very little peptide bond formation was observed in the study.

In more recent work, systems and methods were developed wherein hydroxyl groups and imidazole groups were arranged in small synthetic structures (Roth et al., JACS 127: 325-330, 2005), as well as in nanostructured channels which assured their close proximity (Kisailus et al., PNAS USA, 103(15):5652-5657, 2006). These synthetic structures were designed to mimic the active site of Silicatein, a mineral-synthesizing enzyme that produces filamentous organic/inorganic cores of marine organisms, which utilizes both a serine hydroxyl group and histidine imidazole group for catalysis. Nevertheless, in these studies little or no turnover was observed in either the small synthetic structures or the precision nanostructures. Yet another example involving synthetic synzyme structures is disclosed in U.S.

Pat. No. 6,048,690 to Heller et al., which describes the use of an electric field to enhance catalysis in a basic cysteine-histidine peptide immobilized on an electrode surface as a model for heterogeneous catalysis. However, no activity was observed, suggesting the basic peptide structures still require incorporation of other unique properties.

With regard to other enzyme mechanisms and their catalytic groups, some examples include: (1) Enolase, which catalyzes the conversion of 2-phosphoglycerate to phosphoenol-pyruvate uses a lysine amino group and a glutamate carboxyl group along with $Mg^{2+}$ cations in the catalytic process; (2) Lysozyme, which catalyzes the hydrolysis of glycosidic C—O bonds in polysaccharides uses a glutamate carboxyl and an aspartate carboxyl in the catalytic process; (3) DNA polymerase, which catalyzes the synthesis of DNA uses three aspartate carboxyl groups, two $Mg^{2+}$ cations and deoxynucleotide triphosphates (dNTPs) in the catalytic process; (4) Lactate Dehydrogenase, which catalyzes the reduction of pyruvate to lactate uses two arginine quanidinium groups, a histidine imidazole group and the reduced cofactor/coenzyme nicotinamide adenine dinucleotide (NADH) in the catalytic process; and (5) the water splitting/oxygen-evolving complex in plant photosynthesis utilizes tyrosine hydroxyl groups and four $Mn^{2+}$ cations in this unique and highly important catalytic process. Thus, other catalytic groups which include glutamate carboxyl, the lysine amino, the arginine guanidinium and the tyrosine hydroxyl group; as well as metal cations (e.g., Mg, Mn, Ca) and various coenzymes/cofactors/prosthetic groups (e.g., NADH, FAD, ATP, dNTPs, Heme groups) are involved in enzyme catalysis. Such a diversity of catalytic groups is required in order to carry out the catalysis of a variety of other reactions including oxidation and reduction reactions; group transfer reactions; isomerization reactions; reactions involving the addition or removal of groups from double bonds; ligation reactions involving the formation of C—C, C—S, C—O, and C—N bonds by condensation reactions coupled to ATP or other energy rich molecules; and specialized reactions for photosynthetic driven water-splitting, oxygen evolution, and reductions including hydrogen production.

SUMMARY

The present invention is based in part on the development of novel synthetic catalytic structures, e.g. synthetic polypeptides that are from 6 to 30 amino acids total in length, with catalytic properties. These synthetic catalytic structures are thought to mimic the reaction sites of proteases and include strategically placed catalytic groups, e.g., one or more of a hydroxyl group, a sulfhydryl/thiol group, an imidazole group, and a carboxyl group; and steric groups, e.g., a benzyl group. The catalytic properties of these synthetic catalytic structures can be further improved by the application of controlled external forces, e.g., electric fields. Application of these external forces allows relatively simple synthetic catalytic structures to carry out more efficient dynamic mechanistic movements for efficient catalysis and higher turnover rate.

Disclosed herein are synthetic polypeptides that are from 6 to 30 amino acids total in length that can contain one or more strategically placed histidine or histidine analog, cysteine or cysteine analog, serine or serine analog, aspartic acid or aspartic acid analog, alanine or alanine analog, and/or phenylalanine or phenylalanine analog residues.

In some embodiments, the synthetic polypeptides disclosed herein are from 6 to 30 amino acids total in length and include the amino acid sequence X1-X2-X3-X4-X5 (SEQ ID NO:1). X1, X3, and X5 are independently selected from the group consisting of alanine, an alanine analog, phenylalanine and a phenylalanine analog. In some embodiments, X1, X3, and X5 are independently selected from alanine and phenylalanine. X2 and X4 are independently selected from the group consisting of cysteine, a cysteine analog, serine, a serine analog, histidine, and a histidine analog. In some embodiments, X2 and X4 are independently selected from cysteine, serine, and histidine. When X2 is histidine or a histidine analog, then X4 is cysteine or a cysteine analog, or serine or a serine analog. When X4 is histidine or histidine analog, then X2 is cysteine or a cysteine analog, or serine or a serine analog.

The alanine analog can be selected from the group consisting of β-alanine, dehydroalanine, aminoisobutyric acid, valine and norvaline. The phenylalanine analog can be selected from the group consisting of methylphenylalanine, 1,2,3,4-tetrahydroisoquinoline-3-carboxylic acid, phenylglycine, ethyltyrosine, and methyltyrosine. The cysteine analog can be selected from the group consisting of homocysteine and penicillamine. The serine analog can be selected from the group consisting of methylserine, threonine, 2-amino-3-hydroxy-4-methylpentanoic acid, 3-amino-2-hydroxy-5-methylhexanoic acid, 4-amino-3-hydroxy-6-methylheptanoic acid, and 2-amino-3-hydroxy-3-methylbutanoic acid. The histidine analog can be selected from the group consisting of β-(1,2,3-triazol-4-yl)-DL-alanine, and 1,2,4-triazole-3-alanine.

In some embodiments, SEQ ID NO:1 includes only natural amino acids, e.g., alanine, phenylalanine, cysteine, serine, and histidine. In some embodiments, the synthetic polypeptide can include an amino acid sequence selected from any of SEQ ID NO: 2-37.

In some embodiments, X1, X3, and X5 are alanine or alanine analogs. For example, the synthetic polypeptide can include an amino acid sequence selected from any one of SEQ ID NO: 2, 3, 8, 9, 14, 15, 20, 21, 26, 27, and 28. In some embodiments, X1 and X3 are phenylalanine or phenylalanine analogs. For example, the synthetic polypeptide can include an amino acid sequence selected from any of SEQ ID NO: 4-7, 10-13, 16-19, 22-25, and 29-34.

In some embodiments, the synthetic polypeptides can mimic a cysteine protease and include a catalytic triad consisting of a cysteine or cysteine analog, a histidine or histidine analog, and an aspartic acid or aspartic acid analog. For example, the synthetic polypeptide can include an amino acid sequence selected from any of SEQ ID NO: 8, 10, 12, 14, 16, 18, 20, 22, 24, 26, 27, 29, 30, or 33. In some embodiments, the synthetic polypeptides can mimic a serine protease and include a catalytic triad consisting of a serine or serine analog, a histidine or histidine analog, and an aspartic acid or aspartic acid analog. For example, the synthetic polypeptide can include an amino acid sequence selected from any of SEQ ID NO: 9, 11, 13, 15, 17, 19, 21, 23, 25, 28, 31, 32, or 34.

The synthetic polypeptides can include 6-30, 7-25, 8-20, or 9-15 amino acids total in length. In some embodiments, the synthetic polypeptides include nine amino acids total in length. For example, the synthetic polypeptide can be an amino acid sequence selected from any of SEQ ID NO: 26-34.

In some embodiments, the synthetic polypeptides disclosed herein are from 11 to 30 amino acids total in length and include a "hand-off" structure, which contain two or more histidine or histidine analogs and a proline or proline analog. For example, the synthetic polypeptide can include an amino acid sequence selected from SEQ ID NO: 36 and 37.

In some embodiments, the synthetic polypeptides include a negatively charged C-terminal residue, e.g., aspartic acid, glutamic acid, methyl aspartic acid, methyl glutamic acid, 2-aminoadipic acid, 2-aminoheptanedioic acid, or iminodiacetic acid. In some embodiments, the C-terminal residue of the synthetic polypeptides is aspartic acid. In some embodiments, the synthetic polypeptides include an N-terminal residue selected from the group consisting of glycine, lysine, arginine, citrulline, ornithine, and 2-amino-3-guanidinopropionic acid. In some embodiments, the N-terminal residue of the synthetic polypeptides is glycine, lysine or arginine.

In some embodiments, the synthetic polypeptides can be used in solution for homogenous catalysis applications. For example, these synthetic polypeptides can include an amino acid sequence selected from any of SEQ ID NO: 20-23, 26-29, 31, 33-34 or 36. In some embodiments, the synthetic polypeptide can be immobilized or attached onto a solid surface or support, e.g., a location in an electronic device, through a charged group of the synthetic polypeptide. The charged group can be an N-terminal α-amino group, a C-terminal α-carboxyl group, an ε-amino group of lysine or lysine analog, or a sulfhydryl/thiol group of cysteine or cysteine analog. In some embodiments, the charged group is located on a terminal residue of the synthetic polypeptide. In some embodiments, the charged group is located on a residue within one to five amino acids from a terminus of the synthetic polypeptide, and the charged group does not interfere with the catalytic groups. In some embodiments, the charged group is located on a linker conjugated to the synthetic polypeptide. In some embodiments, the synthetic polypeptide is immobilized or attached onto a solid surface or support through the ε-amino group of a terminal lysine residue. For example, the synthetic polypeptide can include the amino acid sequence of SEQ ID NO: 30 or 32.

In some embodiments, the synthetic polypeptides have an overall net negative charge at a neutral pH, which can allow them to be oriented in solution by electrophoretic movement toward a positive electrode when one dimensional direct current electric field is applied. For example, these synthetic polypeptides can have a negatively charged residue, e.g., aspartic acid, glutamic acid, methyl aspartic acid, methyl glutamic acid, 2-aminoadipic acid, 2-aminoheptanedioic acid, or iminodiacetic acid, at one terminus, and an uncharged or weakly positively charged residue at the other terminus. These synthetic polypeptides can include an amino acid sequence selected from any of SEQ ID NO: 26-34 and 36-37.

In some embodiments, the N-terminus of the synthetic polypeptides is protected and uncharged. For example, the N-terminus is protected by, e.g., an acetyl, tert-butyloxycarbonyl, 9-fluorenylmethyloxycarbonyl, benzoyloxycarbonyl, carbobenzyloxy, p-methoxybenzyl, p-methoxybenzyl carbonyl, benzoyl, benzyl, carbamate, p-methoxyphenyl, 3,4-dimethoxybenzyl, or tosyl group. In some embodiments, the N-terminus of the synthetic polypeptides is protected by acetylation. In some embodiments, the C-terminus of the synthetic polypeptides is protected and uncharged. For example, the C-terminus is protected, e.g., by a methyl, ethyl, benzyl, tert-butyl, silyl, or phenyl group. In some embodiments, both the N-terminus and the C-terminus of the synthetic polypeptides are protected and uncharged.

Disclosed herein are also methods of hydrolyzing an amide or ester bond in a substrate containing an amide or ester moiety using the synthetic polypeptides described herein. The methods include a step of contacting an amide or ester bond containing substrate, e.g., without limitation, a peptide, protein, fatty acid, or glycerol ester, with one or more synthetic polypeptides described herein. The contacting step can be performed under such conditions that a cysteine or cysteine analog, or a serine or serine analog, of the synthetic polypeptides can act as a nucleophilic group to attack the amide or ester bond. Under these conditions, the amide or ester bond in the substrate is cleaved and an acyl-synthetic polypeptide intermediate is formed, e.g., an acyl-sulfhydryl/thiol intermediate (when, for example, cysteine is the nucleophilic group) or an acyl-hydroxyl intermediate (when, for example, serine is the nucleophilic group) is formed. The positively charged imidazole group of the histidine or histidine analog removes the acyl group from the sulfhydryl/thiol or hydroxyl group, and an acyl-imidazole intermediate is formed. The physical proximity between the acyl-imidazole group and the sulfhydryl/thiol or hydroxyl group can be modified to prevent back-attack and facilitate deacylation and turnover of the synthetic polypeptides.

The catalytic rate using the synthetic polypeptides disclosed herein can be further enhanced by using external forces, e.g., electric fields. These external forces, e.g., direct current electric fields, are believed to enable the synthetic polypeptides to carry out the dynamic mechanistic movements necessary for more efficient catalysis and higher turnover. Thus, in some embodiments, a method of hydrolyzing an amide or ester bond in a substrate can include a step of contacting an amide or ester bond containing substrate with one or more synthetic polypeptides described herein; and a step of applying an external force, e.g., an electric field. The contacting step can be performed as described above. The external electric field can be applied to reduce the physical proximity of the acyl-imidazole intermediate and a nucleophilic sulfhydryl/thiol or hydroxyl group of the synthetic polypeptide. The external electrical field can be applied in either one direction or in multiple directions. The application of electrical field can include a single step of applying a directional or an oscillating electric field, or multiple steps of applying directional and oscillating electric fields. When multiple steps of electric field application are utilized, a first directional electric field can be applied for several microseconds to one second to orient the synthetic polypeptide; a second stronger directional electric field can then be applied to position an acyl-sulfhydryl/thiol or acyl-hydroxyl group into close proximity with an imidazole group of the synthetic polypeptide and thereby facilitate formation of an acyl-imidazole intermediate; and then a third oscillating electric field that oscillates at a desired frequency, e.g., from 1 kHz to 1 MHz, can be applied to reduce the physical proximity of the acyl-imidazole intermediate and a nucleophilic sulfhydryl/thiol or hydroxyl group of the synthetic polypeptide.

The present disclosure also includes devices and systems that can be used together with the synthetic polypeptides disclosed herein, e.g., electric field reaction wells, software configured to operate on a computer or processor-driven device or apparatus to control the application of electric fields.

Also provided herein are arrays of synthetic polypeptides. The array can include at least two synthetic polypeptides as described herein. In some embodiments, the array can include at least five synthetic polypeptides. In some embodiments, the array can include at least 15 synthetic polypeptides. In some embodiments, the array of synzymes is attached to a support or substrate, e.g., glass, silicon, or plastic surface, optionally coated with, for example, a porous membrane such as a hydrogel.

Also provided herein are kits of synthetic polypeptides. The kit can include one or more synthetic polypeptides as described herein. The kit can also include instructions for use that include instructions for catalytic applications of the synthetic polypeptides. The kit can also include one or more reaction wells, e.g., electric field cuvettes, to be used with the synzymes. The kit can also include software configured to operate on a computer or processor-driven device or apparatus to control the application of the electric fields to the one or more synthetic polypeptides of the kit.

As used herein, the term "synthetic polypeptide" refers to a polypeptide that is chemically synthesized, but does not refer to naturally occurring or recombinant polypeptides. More specifically, the term "synthetic polypeptide" refers to a polypeptide formed, in vitro, by joining amino acids or amino acid analogs in a particular order, using well known techniques of synthetic organic peptide synthesis to form the peptide bonds.

The term "analog" is used herein to refer to an amino acid molecule that structurally resembles a reference amino acid molecule, but has been modified to modify the stereochemistry of the amino acid to the non-natural D-configuration, and/or to replace one or more specific substituents of the reference amino acid molecule with an alternate substituent.

DETAILED DESCRIPTON

Figure 1:
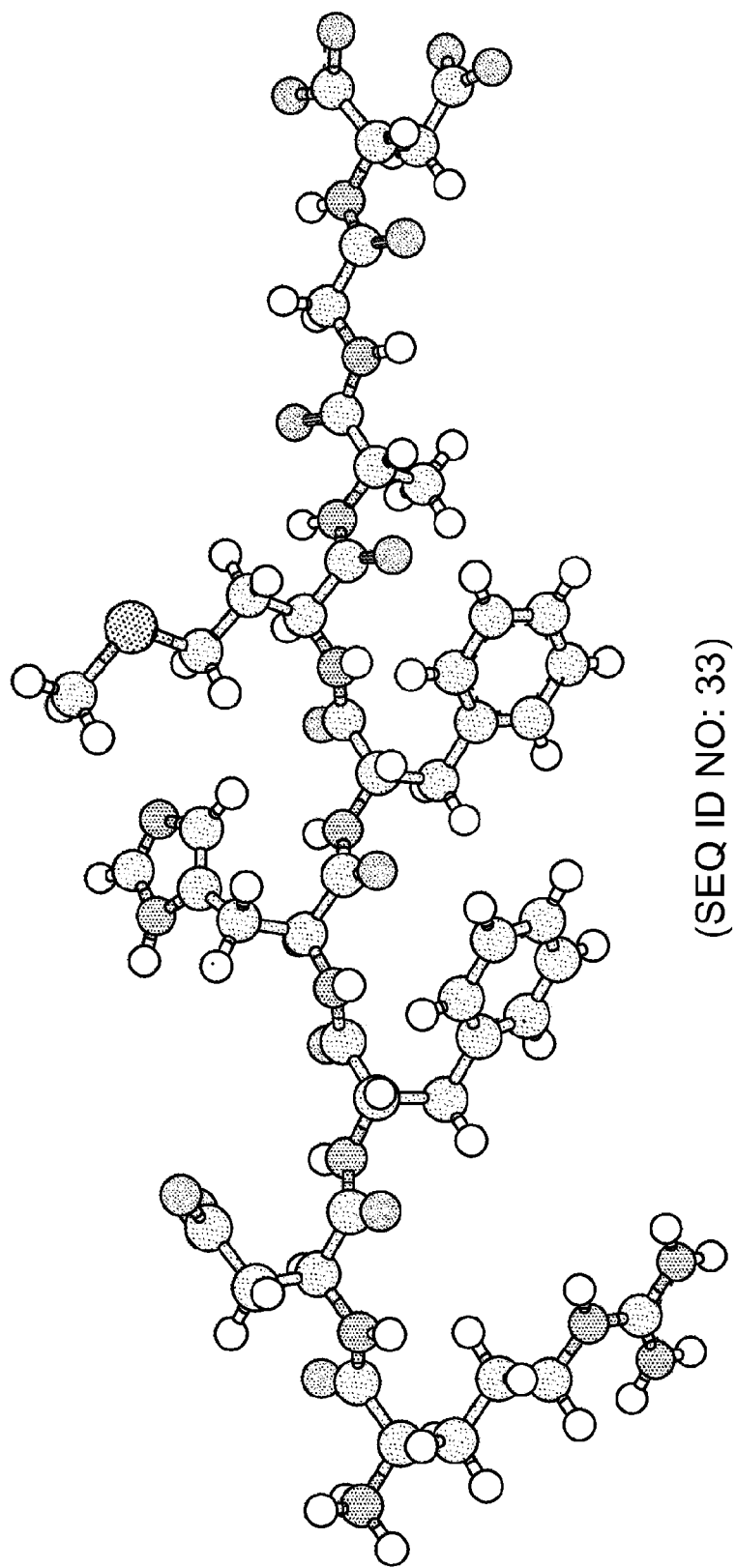
FIG. 1 illustrates an exemplary synthetic polypeptide structure with an amino acid sequence of SEQ ID NO: 33.

The present invention is based in part on the development of novel synthetic catalytic structures, e.g. synthetic polypeptides that are from 6 to 30 amino acids total in length, with catalytic properties. These synthetic catalytic structures are believed to mimic the reaction sites of proteases and include strategically placed catalytic groups, e.g., a hydroxyl group, a sulfhydryl/thiol group, an imidazole group, and a carboxyl group, and steric groups, e.g., a benzyl group. The catalytic properties of these synthetic catalytic structures can be further improved by the application of controlled external forces, e.g., electrical fields, optical, magnetic, acoustical, or mechanical force. Application of these external forces allows relatively simple synthetic catalytic structures to carry out more efficient dynamic mechanistic movements for efficient catalysis and high turnover rate.

Synzymes

Disclosed herein are synthetic polypeptides that are from 6 to 30 amino acids total in length that can contain one or more strategically placed histidine or histidine analog, cysteine or cysteine analog, serine or serine analog, aspartic acid or aspartic acid analog, alanine or alanine analog, and/or phenylalanine or phenylalanine analog residues. These synthetic polypeptides are believed to utilize one or more of the imidazole group of the histidine or histidine analog, the sulfhydryl/thiol group of the cysteine or cysteine analog, the hydroxyl group of the serine or serine analog, and/or the carboxyl group of aspartic acid or aspartic acid analog, to catalyze hydrolysis of amide or ester bond containing substrates, e.g., without limitation, peptides, proteins, fatty acids, or glycerol esters. Placement of an alanine or alanine analog or phenylalanine or phenylalanine analog between the main catalytic residues, e.g., the histidine or histidine analog and the cysteine or cysteine analog, or the histidine or histidine analog and the serine or serine analog, is thought to modulate proximity of the catalytic groups.

As used herein, the term "synthetic polypeptide" refers to a polypeptide that is chemically synthesized, but does not refer to naturally occurring or recombinant polypeptides. More specifically, the term "synthetic polypeptide" refers to a polypeptide formed, in vitro, by joining amino acids or amino acid analogs in a particular order, using well known techniques of synthetic organic peptide synthesis to form the peptide bonds. For example, polypeptides can be synthesized by solid phase techniques (Roberge et al., Science 269: 202-204, 1995), cleaved from the resin, and purified by preparative high performance liquid chromatography (e.g., Creighton, Proteins Structures And Molecular Principles, WH Freeman and Co, New York, 1983). Automated synthesis can be achieved, for example, using an ABI Peptide Synthesizer (Applied Biosystems) in accordance with the instructions provided by the manufacturer.

The term "analog" is used herein to refer to an amino acid molecule that structurally resembles a reference amino acid molecule, but has been modified to modify the stereochemistry of the amino acid to the non-natural D-configuration, and/or to replace one or more specific substituents of the reference amino acid molecule with an alternate substituent.

The present disclosure also relates to synthetic polypeptides that can include other catalytic groups selected from, but not limited to, the amino group of a lysine or lysine analog, the guanidinium group of an arginine or arginine analog, the carboxyl group of a glutamic acid or glutamic acid analog, and the hydroxyl group of a tyrosine or tyrosine analog.

In some embodiments, the synthetic polypeptides disclosed herein are from 6 to 30 amino acids total in length and include the amino acid sequence X1-X2-X3-X4-X5 (SEQ ID NO:1). X1, X3, and X5 are independently selected from the group consisting of alanine, an alanine analog, phenylalanine and a phenylalanine analog. In some embodiments, X1, X3, and X5 are independently selected from alanine and phenylalanine. X2 and X4 are independently selected from the group consisting of cysteine, a cysteine analog, serine, a serine analog, histidine, and a histidine analog. In some embodiments, X2 and X4 are independently selected from cysteine, serine, and histidine. When X2 is histidine or a histidine analog, then X4 is cysteine or a cysteine analog, or serine or a serine analog. When X4 is histidine or histidine analog, then X2 is cysteine or a cysteine analog, or serine or a serine analog.

The alanine analog can be selected from the group consisting of β-alanine, dehydroalanine, aminoisobutyric acid, valine and norvaline. The phenylalanine analog can be selected from the group consisting of methylphenylalanine, 1,2,3,4-tetrahydroisoquinoline-3-carboxylic acid, phenylglycine, ethyltyrosine, and methyltyrosine. The cysteine analog can be selected from the group consisting of homocysteine and penicillamine. The serine analog can be selected from the group consisting of methylserine, threonine, 2-amino-3-hydroxy-4-methylpentanoic acid, 3-amino-2-hydroxy-5-methylhexanoic acid, 4-amino-3-hydroxy-6-methylheptanoic acid, 2-amino-3-hydroxy-3-methylbutanoic acid. The histidine analog can be selected from the group consisting of β-(1,2,3-triazol-4-yl)-DL-alanine, 1,2,4-triazole-3-alanine.

In some embodiments, SEQ ID NO:1 consists of only natural amino acids, e.g., alanine, phenylalanine, cysteine, serine, and histidine. For example, the synthetic polypeptide can include an amino acid sequence selected from any of SEQ ID NO: 2-37 listed in Table 1. In some embodiments, SEQ ID NO:1 includes one or more amino acid analogs as described above. In some embodiments, SEQ ID NO:1 includes only natural amino acids, but the synthetic polypeptide also include other amino acid analogs.

In some embodiments, when X4 is a histidine or histidine analog, X2 is a cysteine or cysteine analog, the synthetic polypeptides can also include an aspartic acid or aspartic acid analog C-terminal to X5 of the core amino acid sequence. In some embodiments, X4 is histidine, X2 is cysteine, the synthetic polypeptide also includes an aspartic acid C-terminal to X5 of SEQ ID NO:1. For example, the synthetic polypeptide can include an amino acid sequence selected from SEQ ID NO: 8 and 10 listed in Table 1. In some embodiments, the synthetic polypeptide consists of an amino acid sequence of SEQ ID NO: 8 or 10.

In some embodiments, when X4 is a histidine or histidine analog, X2 is a serine or serine analog, the synthetic polypeptide can also include an aspartic acid or aspartic acid analog C-terminal to X5 of the core amino acid sequence. In some embodiments, X4 is histidine, X2 is serine, the synthetic polypeptide also includes an aspartic acid C-terminal to X5 of SEQ ID NO:1. For example, the synthetic polypeptide can include an amino acid sequence of SEQ ID NO: 9 or 11 listed in Table 1. In some embodiments, the synthetic polypeptide consists of an amino acid sequence of SEQ ID NO: 9 or 11.

In some embodiments, when X2 is a histidine or histidine analog, X4 is a cysteine or cysteine analog, the synthetic polypeptides can also include an aspartic acid or aspartic acid analog N-terminal to X1 of SEQ ID NO:1. In some embodiments, X2 is histidine, X4 is cysteine, the synthetic polypeptides also includes an aspartic acid residue N-terminal to X1 of SEQ ID NO: 1. For example, the synthetic polypeptides can include the amino acid sequence of SEQ ID NO: 12. In some embodiments, the synthetic polypeptide consists of the amino acid sequence of SEQ ID NO: 12.

In some embodiments, when X2 is a histidine or histidine analog, X4 is a serine or serine analog, the synthetic polypeptides can also include an aspartic acid or aspartic acid analog N-terminal to X1 of the core amino acid sequence. In some embodiments, X2 is histidine, X4 is serine, the synthetic polypeptides also includes an aspartic acid residue N-terminal to X1 of SEQ ID NO:1. For example, the synthetic polypeptide can include the amino acid sequence of SEQ ID NO: 13. In some embodiments, the synthetic polypeptide consists of the amino acid sequence of SEQ ID NO: 13.

In some embodiments, X1, X3, and X5 are alanine or alanine analogs. The small size of alanine or alanine analogs is thought to bring the catalytic groups of X2 and X4 into close proximity. In some embodiments, X1, X3, and X5 are alanine. For example, the synthetic polypeptide can include an amino acid sequence selected from any one of SEQ ID NO: 2, 3, 8, 9, 14, 15, 20, 21, 26, 27, and 28. In some embodiments, the synthetic polypeptide consists of an amino acid sequence selected from any of SEQ ID NO: 2, 3, 8, 9, 14, 15, 20, 21, and 26-28.

In some embodiments, X1 and X3 are phenylalanine or phenylalanine analogs. The bulky side chain of the phenylalanine or phenylalanine analog residue is thought to slightly bend the polypeptide backbone and thereby move the catalytic groups of X2 and X4 into closer proximity when compared to alanine containing polypeptides. In some embodiments, X1 and X3 are phenylalanine. For example, the synthetic polypeptide can include an amino acid sequence selected from any of SEQ ID NO: 4-7, 10-13, 16-19, 22-25, and 29-34. In some embodiments, the synthetic polypeptide consists of an amino acid sequence selected from any of SEQ ID NO: 4-7, 10-13, 16-19, 22-25, or 29-34.

In some embodiments, the synthetic polypeptides can mimic a cysteine protease and include a catalytic triad consisting of a cysteine or cysteine analog, a histidine or histidine analog, and an aspartic acid or aspartic acid analog. In some embodiments, the synthetic polypeptide includes a catalytic triad consisting of a cysteine, a histidine, and an aspartic acid. For example, the synthetic polypeptide can include an amino acid sequence selected from any of SEQ ID NO: 8, 10, 12, 14, 16, 18, 20, 22, 24, 26, 27, 29, 30, or 33. In some embodiments, the synthetic polypeptide consists of an amino acid sequence selected from any of SEQ ID NO: 8, 10, 12, 14, 16, 18, 20, 22, 24, 26, 27, 29, 30, or 33.

In some embodiments, the synthetic polypeptides can mimic a serine protease and include a catalytic triad consisting of a serine or serine analog, a histidine or histidine analog, and an aspartic acid or aspartic acid analog. In some embodiments, the synthetic polypeptide includes a catalytic triad consisting of a serine, a histidine, and an aspartic acid. For example, the synthetic polypeptide can include an amino acid sequence selected from any of SEQ ID NO: 9, 11, 13, 15, 17, 19, 21, 23, 25, 28, 31, 32, or 34. In some embodiments, the synthetic polypeptide consists of an amino acid sequence selected from any of SEQ ID NO: 9, 11, 13, 15, 17, 19, 21, 23, 25, 28, 31, 32, or 34.

The synthetic polypeptides can include 6-30, 7-25, 8-20, or 9-15 amino acids total in length. In some embodiments, the synthetic polypeptides include nine amino acids total in length. For example, the synthetic polypeptide consists of an amino acid sequence selected from any of SEQ ID NO: 26-34.

In some embodiments, the synthetic polypeptides include a negatively charged C-terminal residue, e.g., aspartic acid, glutamic acid, methyl aspartic acid, methyl glutamic acid, 2-aminoadipic acid, 2-aminoheptanedioic acid, or iminodiacetic acid. In some embodiments, the C-terminal residue of the synthetic polypeptides is aspartic acid. In some embodiments, the synthetic polypeptides include an N-terminal residue selected from the group consisting of glycine, lysine, arginine, citrulline, ornithine, and 2-amino-3-guanidinopropionic acid. In some embodiments, the N-terminal residue of the synthetic polypeptides is glycine, lysine or arginine.

In some embodiments, the synthetic polypeptides can be used in solution for homogenous catalysis applications. For example, these synthetic polypeptides can include an amino acid sequence selected from any of SEQ ID NO: 20-23, 26-29, 31, 33-34 or 36. In some embodiments, the synthetic polypeptide consists of an amino acid sequence selected from any of SEQ ID NO: 20-23, 26-29, 31, 33-34 or 36. FIG. 1 shows the structure of a synthetic polypeptide having the amino acid sequence of SEQ ID NO: 33, which has a catalytic triad consisting of a cysteine, a histidine, and an aspartic acid.

In some embodiments, the synthetic polypeptide can be immobilized or attached onto a solid surface or support, e.g., a location in an electronic device, through a charged group of the synthetic polypeptide. The charged group can be an N-terminal α-amino group, a C-terminal α-carboxyl group, an ε-amino group of lysine or lysine analog, or a sulfhydryl/thiol group of cysteine or cysteine analog. In some embodiments, the charged group is located on a terminal residue of the synthetic polypeptide. In some embodiments, the charged group is located on a residue within one to five amino acids from a terminus of the synthetic polypeptide, and the charged group does not interfere with the catalytic groups. In some embodiments, the charged group is located on a linker conjugated to the synthetic polypeptide. In some embodiments, the synthetic polypeptide is immobilized or attached onto a solid surface or support through the ε-amino group of a terminal lysine residue. For example, the synthetic polypeptide can include the amino acid sequence of SEQ ID NO: 30 or 32.

In some embodiments, the synthetic polypeptides have an overall net negative charge at a neutral pH, which can allow them to be oriented in solution by electrophoretic movement toward the positive electrode when one dimensional direct current electric field is applied. For example, these synthetic polypeptides can have a negatively charged residue, e.g., aspartic acid, glutamic acid, methyl aspartic acid, methyl glutamic acid, 2-aminoadipic acid, 2-aminoheptanedioic acid, or iminodiacetic acid, at one terminus, and an uncharged or weakly positively charged residue at the other terminus. These synthetic polypeptides can include an amino acid sequence selected from any of SEQ ID NO: 26-34 and 36-37. In some embodiments, the synthetic polypeptide consists of an amino acid sequence selected from any of SEQ ID NO: 26-34 and 36-37.

In some embodiments, the N-terminus of the synthetic polypeptides is protected and uncharged. For example, the N-terminus is protected by, e.g., an acetyl, tert-butyloxycarbonyl, 9-fluorenylmethyloxycarbonyl, benzoyloxycarbonyl, carbobenzyloxy, p-methoxybenzyl, p-methoxybenzyl carbonyl, benzoyl, benzyl, carbamate, p-methoxyphenyl, 3,4-dimethoxybenzyl, or tosyl group. In some embodiments, the N-terminus of the synthetic polypeptides is protected by acetylation. In some embodiments, the C-terminus of the synthetic polypeptides is protected and uncharged. For example, the C-terminus is protected, e.g., by a methyl, ethyl, benzyl, tert-butyl, silyl, or phenyl group. In some embodiments, both the N-terminus and the C-terminus of the synthetic polypeptides are protected and uncharged.

Exemplary synthetic polypeptide sequences are provided in Table 1:

TABLE 1

| Exemplary Synthetic Polypeptide Sequences | |
|---|---|
| Ala-Cys-Ala-His-Ala | SEQ ID NO: 2 |
| Ala-Ser-Ala-His-Ala | SEQ ID NO: 3 |
| Phe-Cys-Phe-His-Ala | SEQ ID NO: 4 |
| Phe-Ser-Phe-His-Ala | SEQ ID NO: 5 |
| Phe-His-Phe-Cys-Ala | SEQ ID NO: 6 |
| Phe-His-Phe-Ser-Ala | SEQ ID NO: 7 |
| Ala-Cys-Ala-His-Ala-Asp | SEQ ID NO: 8 |
| Ala-Ser-Ala-His-Ala-Asp | SEQ ID NO: 9 |
| Phe-Cys-Phe-His-Ala-Asp | SEQ ID NO: 10 |
| Phe-Ser-Phe-His-Ala-Asp | SEQ ID NO: 11 |
| Asp-Phe-His-Phe-Cys-Ala | SEQ ID NO: 12 |
| Asp-Phe-His-Phe-Ser-Ala | SEQ ID NO: 13 |
| Ala-Ala-Cys-Ala-His-Ala-Asp | SEQ ID NO: 14 |
| Ala-Ala-Ser-Ala-His-Ala-Asp | SEQ ID NO: 15 |
| Ala-Phe-Cys-Phe-His-Ala-Asp | SEQ ID NO: 16 |
| Ala-Phe-Ser-Phe-His-Ala-Asp | SEQ ID NO: 17 |
| Asp-Phe-His-Phe-Cys-Ala-Gly | SEQ ID NO: 18 |
| Asp-Phe-His-Phe-Ser-Ala-Gly | SEQ ID NO: 19 |
| Gly-Ala-Ala-Cys-Ala-His-Ala-Asp | SEQ ID NO: 20 |
| Gly-Ala-Ala-Ser-Ala-His-Ala-Asp | SEQ ID NO: 21 |
| Gly-Ala-Phe-Cys-Phe-His-Ala-Asp | SEQ ID NO: 22 |
| Gly-Ala-Phe-Ser-Phe-His-Ala-Asp | SEQ ID NO: 23 |
| Asp-Phe-His-Phe-Cys-Ala-Gly-Asp | SEQ ID NO: 24 |
| Asp-Phe-His-Phe-Ser-Ala-Gly-Asp | SEQ ID NO: 25 |
| Gly-Gly-Ala-Ala-Cys-Ala-His-Ala-Asp | SEQ ID NO: 26 |
| Arg-Gly-Ala-Ala-Cys-Ala-His-Ala-Asp | SEQ ID NO: 27 |
| Arg-Gly-Ala-Ala-Ser-Ala-His-Ala-Asp | SEQ ID NO: 28 |
| Arg-Gly-Ala-Phe-Cys-Phe-His-Ala-Asp | SEQ ID NO: 29 |
| Lys-Gly-Ala-Phe-Cys-Phe-His-Ala-Asp | SEQ ID NO: 30 |
| Arg-Gly-Ala-Phe-Ser-Phe-His-Ala-Asp | SEQ ID NO: 31 |
| Lys-Gly-Ala-Phe-Ser-Phe-His-Ala-Asp | SEQ ID NO: 32 |
| Arg-Asp-Phe-His-Phe-Cys-Ala-Gly-Asp | SEQ ID NO: 33 |
| Arg-Asp-Phe-His-Phe-Ser-Ala-Gly-Asp | SEQ ID NO: 34 |

TABLE 1-continued

Exemplary Synthetic Polypeptide Sequences

His-Gly-Gly-Pro-Gly-Gly-His-Gly-Cys-Gly-Asp    SEQ ID NO: 35

Arg-Gly-His-Gly-Gly-Pro-Gly-Gly-His-Gly-Cys-Gly-Asp    SEQ ID NO: 36

Arg-Gly-His-Phe-Cys-Gly-Pro-Gly-His-Gly-His-Gly-Asp    SEQ ID NO: 37

Some prior art peptides that contain catalytic groups such as a serine-hydroxyl or cysteine-sulfhydryl/thiol, a histidine-imidazole, and an aspartate-carboxyl do not exhibit efficient catalytic properties due to ineffective turnover. This is thought to be primarily due to the back-attack problem, where after an acetyl group transfer from a cysteine sulfhydryl/thiol group to a histidine imidazole group occurs, the primary nucleophile (the sulfhydryl/thiol group here) re-attacks the acetyl-imidzole group before it can deacetylate (Heller, et al., JACS; 99(8): 2780, 1977; Kisailus, et al., PNAS, 103(15): 5652-5657, 2006; Carrea, et al., Trends in Biotechnology 23(10):507-1323(10), 2005). As used herein, the term "acylation" (and in some embodiments, "acetylation" if the substrate includes an acetate moiety) refers to the nucleophilic attack (i.e., via the nucleophilic hydroxyl or sulfhydryl/thiol group on the synthetic polypeptide) on the ester or amide bond of the substrate, thus breaking the amide or ester bond and forming the acyl-synthetic polypeptide intermediate structure (i.e., the acylated hydroxyl or sulfhydryl/thiol group) after an amide or ester-containing substrate is contacted with the synthetic polypeptide. As used herein, the term "deacylation" (and in some embodiments, "deacetylation" if the substrate includes an acetate moiety) refer to hydrolyzing the acyl-synthetic polypeptide intermediate and restoring the synthetic polypeptide to its original state (also referred to as "turnover").

Figure 2:
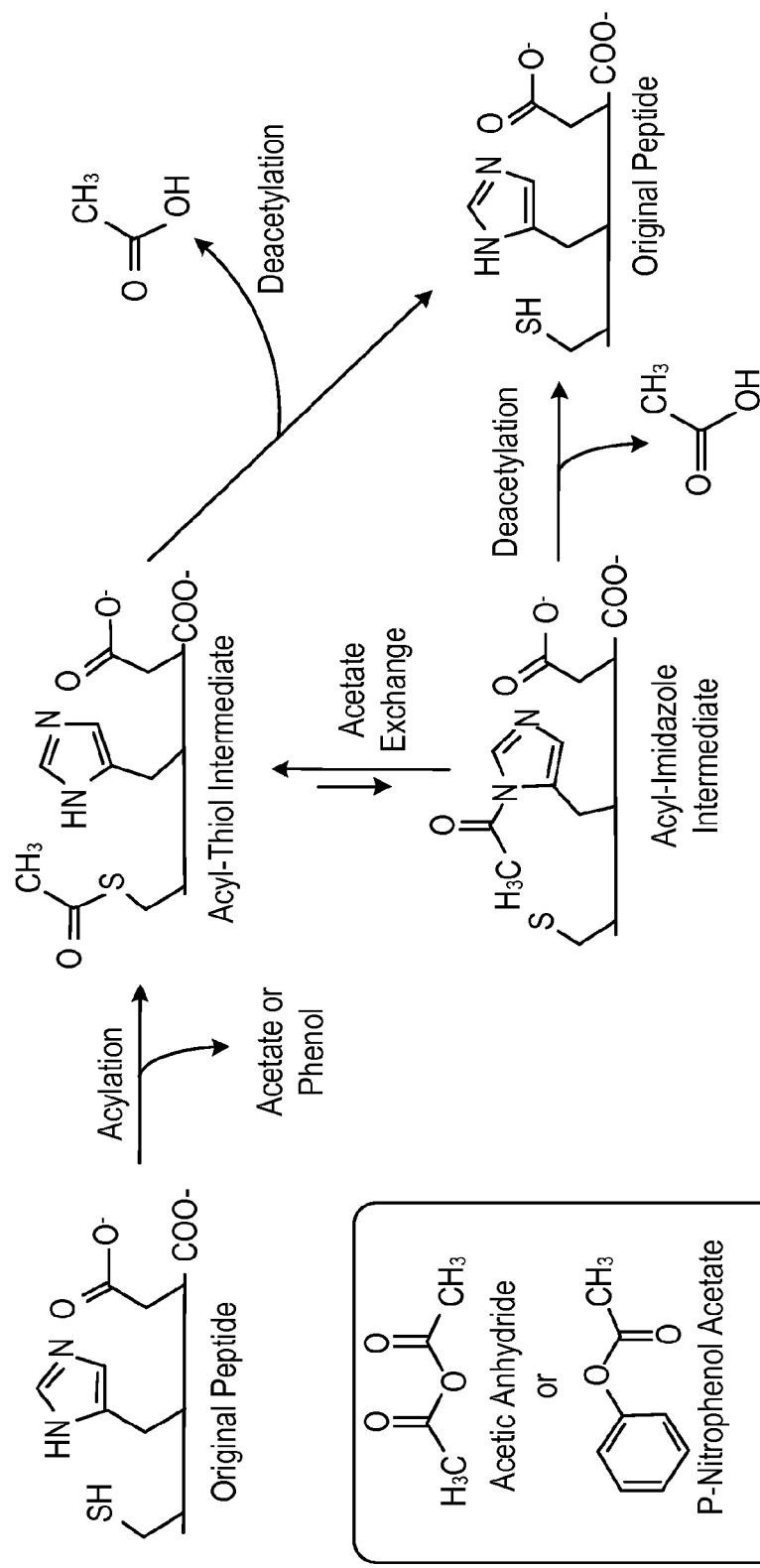
FIG. 2 illustrates an exemplary back-attack problem.

FIG. 2 illustrates the back-attack problem. The synthetic polypeptide in FIG. 2 contains a triad consisting of a cysteine, a histidine, and an aspartic acid residue. The synthetic polypeptide reacts with an ester bond containing substrate such as Acetic Anhydride (AA) or p-Nitrophenol Acetate (pNA). The sulfhydryl/thiol group of the synthetic polypeptide attacks the ester bond in the substrate and forms an acyl-sulfhydryl/thiol intermediate. The product of the cleaved substrate is either a phenol or acetate. The acyl-sulfhydryl/thiol bond is strong, thus deacylation of the acyl-sulfhydryl/thiol group does not usually occur. Instead, the positively charged imidazole group of the histidine residue removes the acyl group from the sulfhydryl/thiol group, and an acyl-imidazole intermediate is formed. Ideally, deacylation of the acyl-imidazole intermediate occurs and restores the synthetic polypeptide to its original state, i.e. turnover of the synthetic polypeptide. However, this can be hindered because of the back attack by the sulfhydryl/thiol group, which causes the acyl group to exchange between the sulfhydryl/thiol and imidazole groups, with the acyl-sulfhydryl/thiol intermediate being more favored than the acyl-imidazole intermediate. Thus this back-attack by the sulfhydryl/thiol group on the acyl-imidazole group prevents the synthetic polypeptide from turning over.

The dynamic movements that can be achieved by the synthetic polypeptides disclosed herein are thought to mimic the mechanistic properties found in real enzymes even without highly complex three dimensional structures. This is achieved by strategically placing the key catalytic groups and steric groups such that the catalytic groups are in close proximity at certain times and under certain conditions, while the proximity can be reduced at other times and under other conditions to eliminate the back-attack problem and facilitate turnover of the synthetic polypeptide. Thus it is within the scope of the present disclosure to provide appropriate steric groups in the structure to produce more favorable proximity of catalytic groups and/or to produce two and three dimensional conformations for inducing improved dynamic mechanistic properties when external forces (e.g. electric fields) are applied.

In some embodiments, the synthetic polypeptides disclosed herein are from 11 to 30 amino acids total in length and include a "hand-off" structure, which contain two or more histidine or histidine analogs and a proline or proline analog. For example, the synthetic polypeptide can include the amino acid sequence of SEQ ID NO: 36 that includes two histidine residues and a proline residue, or the amino acid sequence of SEQ ID NO: 37 that includes three histidine residues and a proline residue. In some embodiments, the synthetic polypeptide consists of an amino acid sequence selected from SEQ ID NO: 36 and 37. The proline or proline analog is believed to create a turn in the polypeptide backbone and bring the second and/or third histidine or histidine analog into close proximity with the first histidine or histidine analog. The second and/or third histidine or histidine analog can be positioned in a way such that when the acyl-imidazole intermediate forms on the first histidine or histidine analog, the second and/or third histidine or histidine analogs competes with the sulfhydryl/thiol group for binding to the acyl group and to move the acyl group further away from the sulfhydryl/thiol group to avoid it transferring back to the sulfhydryl/thiol group. This is advantageous because there are additional forces attracting the acyl group once the initial transfer occurs. The hand-off structure reduces the back-attack from the sulfhydryl/thiol group, and enhances deacylation rates. Permutations of the hand-off structure are possible by using D-amino acids or other unnatural synthetic amino acids. The unnatural synthetic amino acids can provide more flexibility to design structures with better proximity arrangements.

Figure 3:
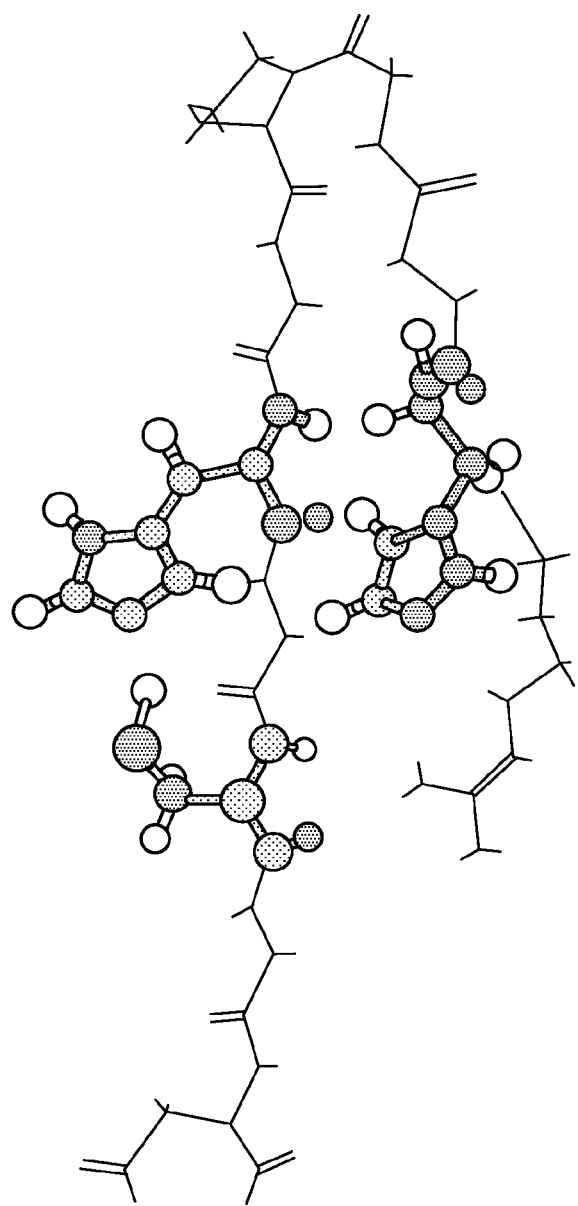
FIG. 3 illustrates an exemplary synthetic polypeptide structure with an amino acid sequence of SEQ ID NO: 36.

The synthetic polypeptides with a hand-off structure can include 11-30, 12-25, or 13-20 amino acids total in length. FIG. 3 shows one such hand-off synthetic polypeptide with the amino acid sequence of SEQ ID NO: 36. The proline residue is thought to make a secondary "V" structure in the polypeptide that brings the second histidine into close proximity with the first histidine. The C-terminal negatively charged aspartic acid residue and N-terminal positively charged arginine group are thought to stabilize the "V" structure by their electrostatic interaction, but also allow a pulsed electric field to flex the structure to open and close, varying the interaction distances between the cysteine, the first histidine and the second histidine residues.

In addition to synthetic polypeptides, it is also within the scope of the present disclosure to design synzymes using other synthetic molecules, polymers or nanostructures which can provide reactive sulfhydryl/thiol/groups, hydroxyl groups, imidazole groups, carboxyl groups, amino groups or any other useful chemical group.

For example, the synthetic catalytic structures can be based on modified DNA (e.g. hairpins) or modified RNA 3D structures. DNA and RNA can also be used to provide hybridization templates to bring catalytic groups, reactants and substrates into close proximity. These synthetic DNA/RNA catalytic structures can be designed such that the application of external forces (e.g., electric fields) can produce efficient catalysis and turnover.

Figure 4:
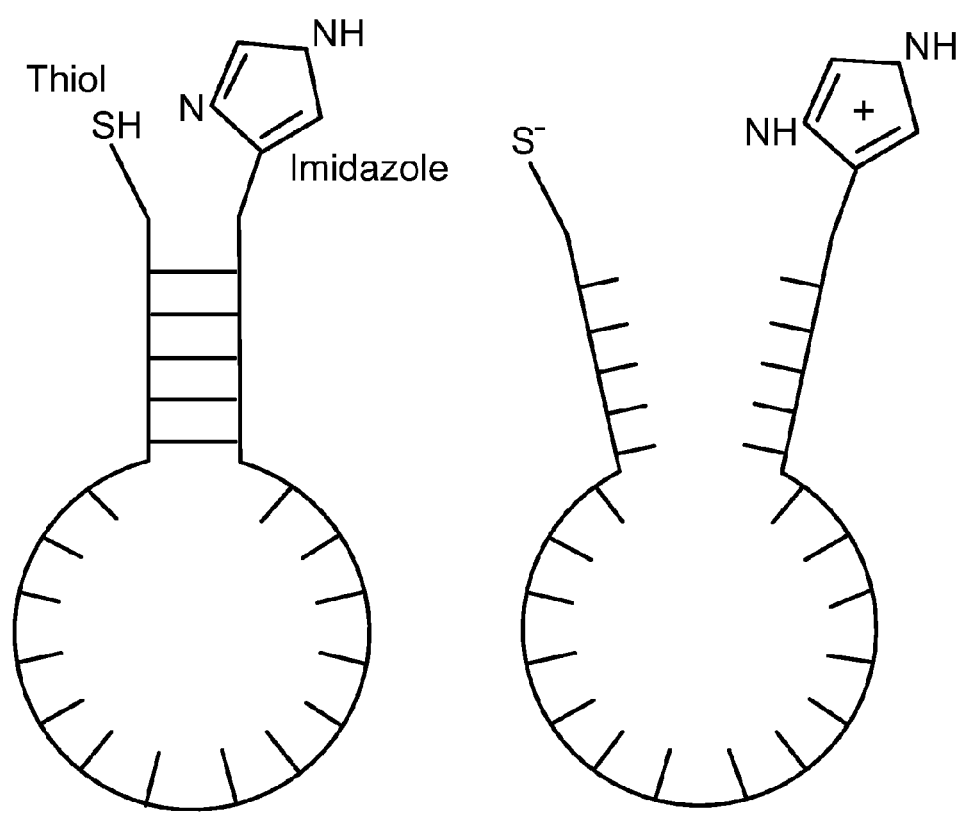
FIG. 4 illustrates an exemplary design for achieving efficient catalysis using DNA and/or RNA derived synzyme structures.

FIG. 4 illustrates an exemplary design for using a modified DNA and/or RNA "hairpin" synzyme structures for achieving efficient catalysis in various applications. In this example, the 3' and 5' terminal positions are modified with a sulfhydryl/thiol group and an imidazole group for amide or ester bond hydrolysis. Directional electric fields can be used to induce opening and closing of the hairpin structure enhancing acylation and deacylation catalytic reactions. This represents just one example of how modified DNA and RNA structures can be used as synzymes in a wide variety of reactions and for many applications.

Figure 9:
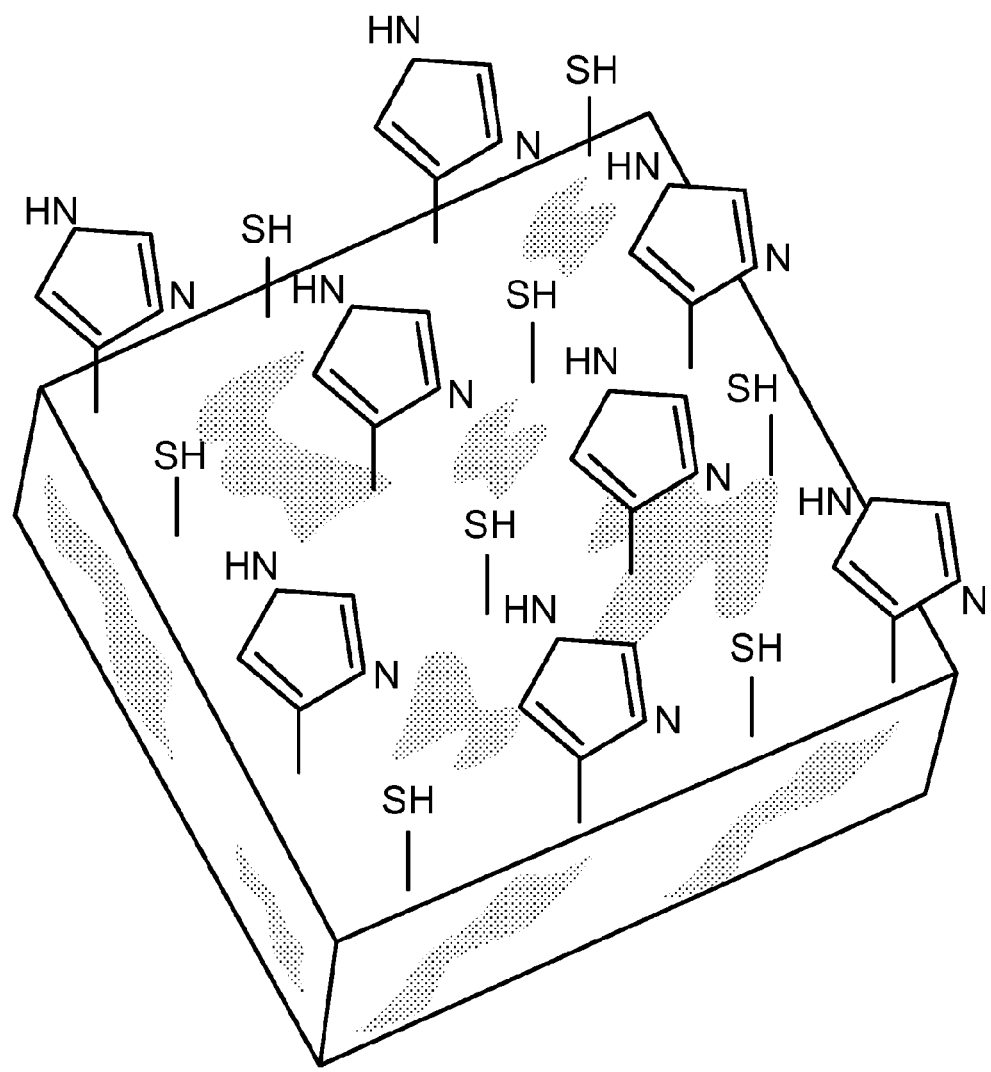
FIG. 9 illustrates an exemplary design of a DNA origami structure for attachment of synzymes for achieving efficient catalysis.

FIG. 9 illustrates an exemplary design of a DNA origami structure for attachment of synzymes for achieving efficient catalysis. More specifically, this shows one way in which DNA origami can be used to create surfaces where synzymes and catalytic groups can be precisely positioned for enhanced catalysis and turnover when external forces such as electric fields are applied.

It is also within the scope of the present disclosure to incorporate other groups (charged, polar, apolar) into the synzyme structures which increase the binding affinity of substrate molecules to the catalytic site through charge, hydrogen bonding, hydrophobic binding and van der Waals interactions, i.e., create specific binding sites. All these features are designed to: (1) accelerate the substrate binding event; (2) transform the key catalytic groups into active nucleophiles, electrophiles, general acid/bases for catalyzing hydrolysis of substrates, as well as other reactive groups for catalyzing the oxidation/reduction, isomerization, group transfer; ligation reactions of specific substrate molecules; and hydrogen production; (3) produce a high turnover of the substrate into product, allowing efficient regeneration of the catalyst; and (4) have the synzyme's dynamic catalytic mechanistic properties augmented and enhanced by application of external forces.

Thus the novel synthetic catalytic structures or synzymes disclosed herein include, but are not limited to, synthetic peptides (linear, cyclic, curved/bowed, V-shaped, hairpin), synthetic macromolecules (cyclodextrins, synthetic polymers, biopolymers), modified DNA (hairpins, origami structures), modified RNA (3D structures), modified existing proteins, dendrimers, micelles, lipid vesicles, nanoparticles, carbon nanotubes, other nanostructures, microstructures and macrostructures (including but not limited to, class, silicon, polymer, plastic and ceramic structures with electrodes), as well as various combinations of these entities and structures. These novel synzyme structures are designed with strategically placed catalytic groups and additional positively or negatively charged groups within the structure; and/or positively or negatively charged entities bound to the synthetic synzyme structure.

Method of Hydrolyzing Substrates Using the Synzymes

Disclosed herein are also methods of hydrolyzing an amide or ester bond in a substrate containing an amide or ester moiety using the synthetic polypeptides described herein. The methods include a step of contacting an amide or ester bond containing substrate, e.g., a peptide, protein, fatty acid, or glycerol ester, with one or more synthetic polypeptides described herein. The contacting step can be performed under such conditions that a cysteine or cysteine analog, or a serine or serine analog, of the synthetic polypeptides can act as a nucleophilic group to attack the amide or ester bond. Under these conditions, the amide or ester bond in the substrate is cleaved and an acyl-synthetic polypeptide intermediate is formed, e.g., an acyl-sulfhydryl/ thiol intermediate (when, for example, cysteine is the nucleophilic group) or an acyl-hydroxyl intermediate (when, for example, serine is the nucleophilic group) is formed. The positively charged imidazole group of the histidine or histidine analog removes the acyl group from the sulfhydryl/ thiol or hydroxyl group, and an acyl-imidazole intermediate is formed. The physical proximity between the acyl-imidazole group and the sulfhydryl/thiol or hydroxyl group can be modified to prevent back-attack and facilitate deacylation and turnover of the synthetic polypeptides.

The catalytic rate using the synthetic polypeptides disclosed herein can be further enhanced by using external forces, e.g., electric fields. These external forces, e.g., direct current electric fields, are believed to enable the synthetic polypeptides to carry out the dynamic mechanistic movements necessary for more efficient catalysis and higher turnover. Thus in some embodiments, a method of hydrolyzing an amide or ester bond in a substrate can include a step of contacting an amide or ester bond containing substrate with one or more synthetic polypeptides described herein; and a step of applying an external force, e.g., an electric field. The contacting step can be performed as described above. The external electric field can be applied to reduce the physical proximity of the acyl-imidazole intermediate and a nucleophilic sulfhydryl/thiol or hydroxyl group of the synthetic polypeptide. The external electrical field can be applied in either one direction or in multiple directions. The application of electrical field can include a single step of applying a directional or an oscillating electric field, or multiple steps of applying directional and oscillating electric fields. For example, when multiple steps of electric field application are utilized, a first directional electric field can be applied for several microseconds to one second to orient the synthetic polypeptide; a second stronger directional electric field can then be applied to position an acyl-sulfhydryl/thiol or acyl-hydroxyl group into close proximity with an imidazole group of the synthetic polypeptide and thereby facilitate formation of an acyl-imidazole intermediate; and then a third oscillating electric field that oscillates at a desired frequency, e.g., from 1 kHz to 1 MHz, can be applied to reduce the physical proximity of the acyl-imidazole intermediate and a nucleophilic sulfhydryl/ thiol or hydroxyl group of the synthetic polypeptide. Thus the application of one or more electric fields can be used to facilitate turnover of the synthetic polypeptides.

It is within the scope of the present disclosure to use electric fields and/or other external forces to: (1) produce more active nucleophiles or electrophiles by changing pKa; (2) prevent back-attack in oxidation/reduction and other reactions; (3) orient synthetic synzyme structures for more efficient catalysis for homogeneous (in solution) catalysis; (4) flex and/or open and close synthetic synzyme structures for more efficient catalysis and turnover; (5) concentrate substrate molecules at active site locations; and (6) rapidly remove product molecules from the active site locations.

Figure 6:
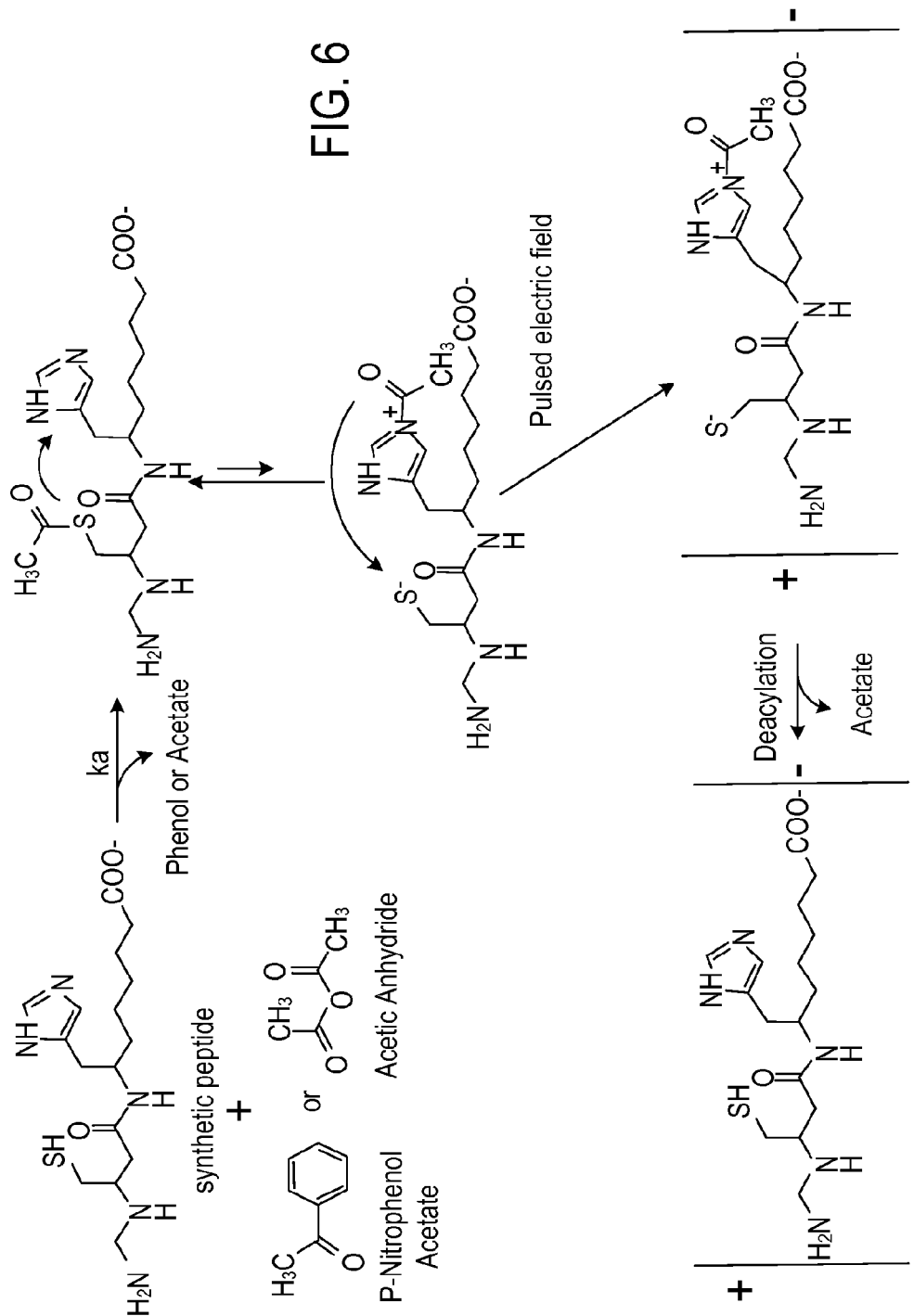
FIG. 6 illustrates an example of applying an electrical field to prevent back-attack and achieve complete deacylation and turnover of a polypeptide synzyme in solution for homogeneous catalysis applications.

FIG. 6 shows a basic scheme for using directional DC/AC electric fields (continuous and/or pulsed and/or oscillated with polarity reversal) with the various synthetic polypeptides disclosed herein for homogeneous catalysis applications in solution. The synthetic polypeptide in FIG. 6 contains a catalytic triad consisting of a cysteine, a histidine, and an aspartic acid residue. The synthetic polypeptide reacts with an ester bond containing substrate such as Acetic Anhydride (AA) or p-Nitrophenol Acetate (pNA). The sulfhydryl/thiol group of the synthetic polypeptide attacks the ester bond in the substrate and forms an acyl-sulfhydryl/thiol intermediate. The product of the cleaved substrate is either a phenol or an acetate. In practice, these types of synthetic polypeptides are designed to carry out the hydrolysis of amide bonds in proteins and polypeptides, as well as ester bonds in synthetic molecules and biomolecules. The acetylation can be calculated as a second order reaction using the following equation:

$$k_a = (\text{initial rate} - \text{spontaneous rate})/[\text{catalyst}][\text{substrate}].$$

As described above, due to the back attack by the sulfhydryl/thiol group, deacylation of the acyl-sulfhydryl/thiol or acyl-imidazole intermediates and turnover of the synthetic polypeptides are hindered. To solve this problem, a DC/AC electrical field can be introduced. For example, a first directional DC electric field can be applied for a very short period of time (microsecond to second) to orient the polypeptide synzyme in solution. Next, a stronger second directional DC electric field can be applied with a polarity that causes the cysteine sulfhydryl/thiol group or serine hydroxyl group to come into close proximity with the histidine imidazole group, allowing the imidazole group to abstract the hydrogen from the sulfhydryl/thiol or hydroxyl group. This lowers the pKa of the sulfhydryl/thiol or hydroxyl group and greatly increases its nucleophilicity and ability to react with the amide or ester bond in the substrate (i.e., enhanced acylation). Finally, the polarity of the DC electric field can be reversed and then oscillated at a frequency, e.g., from 1 kHz to 1 MHz, that allows the acyl group to transfer to histidine imidazole group, but reduces back-attack by the sulfhydryl/thiol or hydroxyl group, allowing subsequent deacylation of the acyl-imidazole intermediate and turnover of the synthetic polypeptide (i.e., enhanced deacylation and turnover). This represents just one example of the many different scenarios where DC/AC electric fields in continuous, and/or pulsed, and/or oscillated with polarity reversal modes can be used to improve catalysis and turnover of the synzymes disclosed herein for homogeneous catalysis applications in solution.

Figure 7:
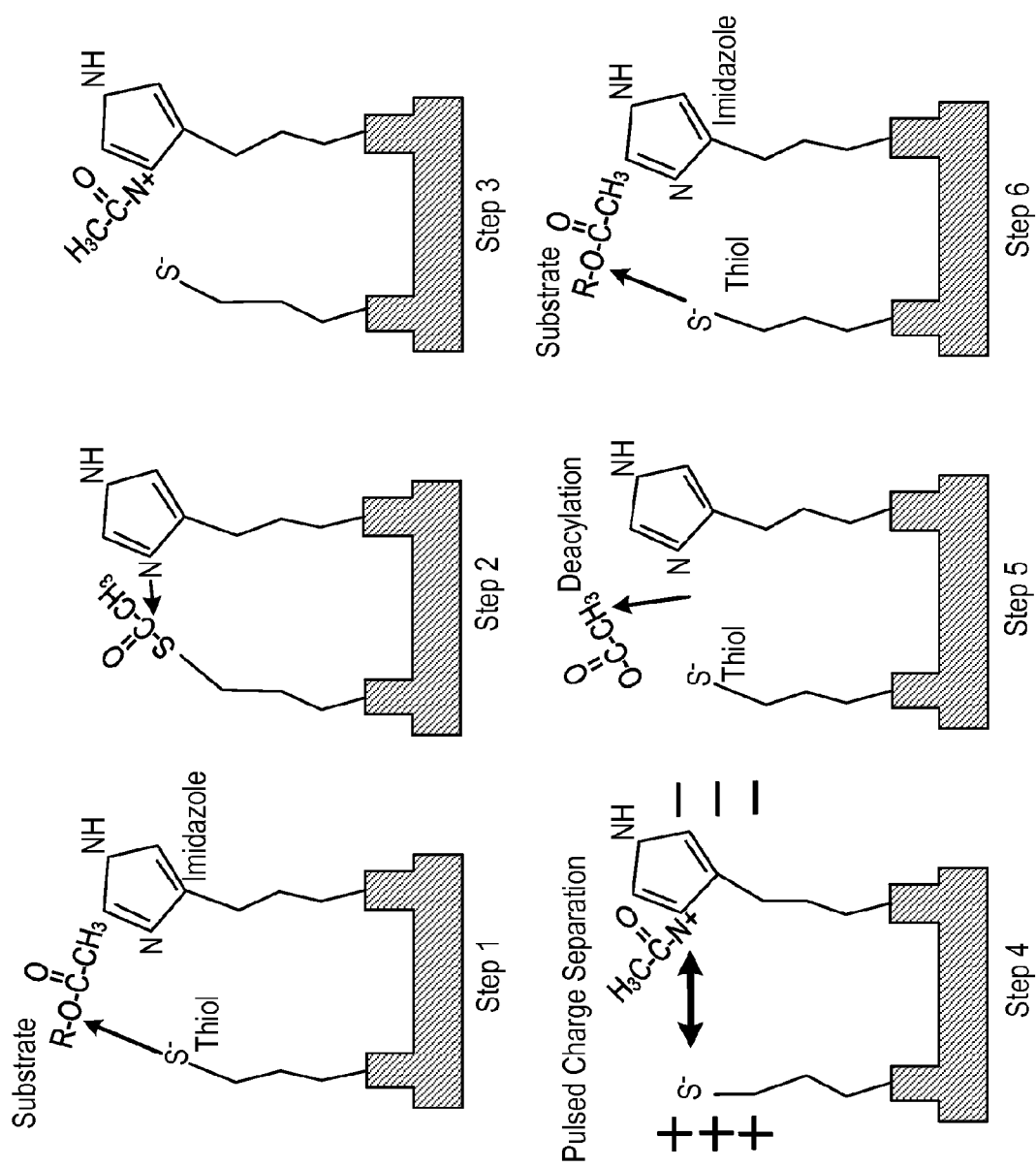
FIG. 7 illustrates an example of applying an electrical field to prevent back-attack and achieve complete deacylation and turnover of a polypeptide synzyme attached to a support for heterogeneous catalysis applications.

FIG. 7 shows one example of how DC/AC electric fields in continuous and/or pulsed and/or oscillated with polarity reversal modes can overcome back-attack in a synthetic polypeptide structure immobilized on a support for heterogeneous catalysis applications. A first directional DC electric field can be applied for a very short period of time (microsecond to second), to orient the catalytic groups on the support. Next, a stronger second directional DC electric field (across the support) can be applied with a polarity that causes the cysteine sulfhydryl/thiol group or serine hydroxyl group to come into close proximity with the histidine imidazole group, allowing the imidazole group to abstract the hydrogen from the sulfhydryl/thiol or hydroxyl group. This lowers the pKa of the sulfhydryl/thiol or hydroxyl group and greatly increases its nucleophilicity and ability to react with the amide or ester bond in the substrate (i.e., enhanced acylation). Finally, the polarity of the DC electric field can be reversed and then oscillated at a frequency, e.g., from 1 kHz to 1 MHz, that allows the acyl group to transfer to histidine imidazole group, but reduces back-attack by the sulfhydryl/thiol or hydroxyl group, allowing subsequent deacylation of the acyl-imidazole intermediate and turnover of the synthetic polypeptides (i.e., enhanced deacylation and turnover). This represents just one example of the many different scenarios where DC/AC electric fields in continuous, and/or pulsed, and/or oscillated with polarity reversal modes, as well as different electrode arrangements can be used to improve catalytic efficiency and turnover of synzymes attached to supports for heterogeneous catalysis applications.

For heterogeneous catalysis applications, the electric field can also be used to produce a high concentration of substrate molecules at the catalytic surface. The electric fields can be applied in any orientation (X, Y, or Z) around the synzymes on the support. For certain applications, the synzymes are directly immobilized or attached to the electrode surface, or to a thin porous (e.g. hydrogel) layer covering the electrode.

Figure 8:
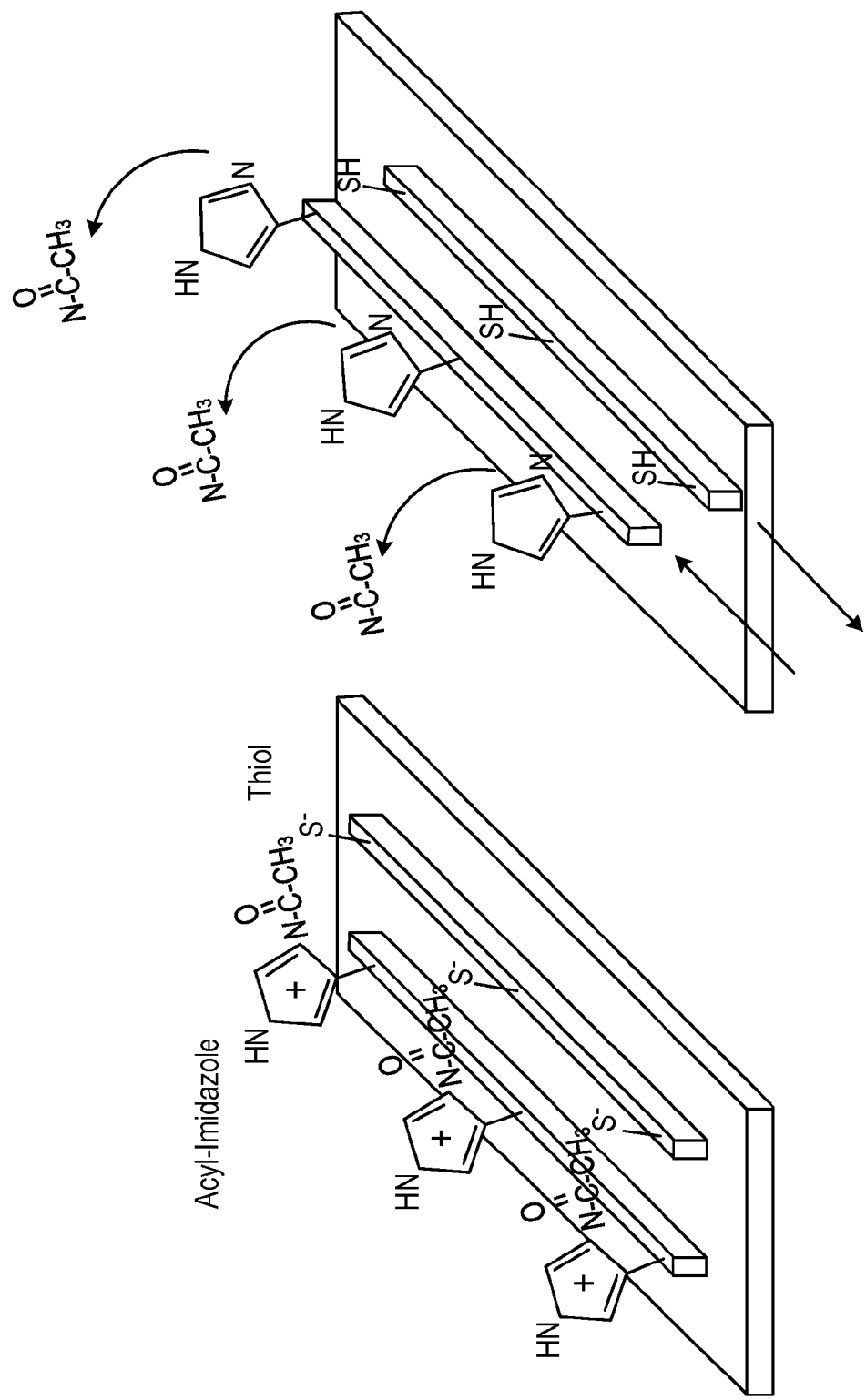
FIG. 8 illustrates an exemplary design of a mechanical synzyme nanostructure.

FIG. 8 shows an exemplary design of a mechanical synzyme nanostructure for achieving efficient catalysis. This nanomechanical structure includes linear arrangements of sulfhydryl/thiol or hydroxyl groups and imidazole groups in close proximity. Mechanical movement of the linear nanostructures allows the groups to be moved closer together or further apart, thus producing dynamic mechanistic properties for catalysis and turnover. The movement of the structure can be produced by external mechanical forces or induced by electric fields. The mechanical forces can be applied by a device, e.g., a microelectromechanical device, which moves at a nanometer or micron scale. The mechanical forces can also be applied through a magnetic field, or by optical, ultrasound, chemical, hydraulic means.

Devices and Systems Used with the Synzymes

The present disclosure also includes devices and systems that can be used together with the synthetic polypeptides disclosed herein. These devices and systems can provide controlled application of external forces to synzymes to produce more efficient catalysis. The external forces include but are not limited to electric field, electronic, electrical, electrophoretic, dielectrophoretic (DEP), electrokinetic, electroosmotic, optical, photonic, magnetic, acoustical, fluidic, mechanical, thermal forces as well as various combinations of these external forces. Devices with one, two or three dimensional (2D/3D) arrangements of electrode structures (e.g. Pt, Pd, Au, carbon) that allow for application of direct current (DC) or alternating current (AC) electric fields in continuous and/or pulsed and/or oscillated with polarity reversal modes to be applied to the synzymes in solution or on supports. In the case of using DC and/or AC electric fields for synthetic synzyme structures on supports (heterogeneous catalysis), this would include, but not be limited to, the nano/micro and macroelectrode structures (e.g., Pt, Pd, Au, carbon) on supports (e.g., glass, silicon, plastic) which can be over-layered with porous structures (e.g., hydrogels) to which the synthetic synzyme structures are attached. These devices can have one dimensional (1D), 2D or 3D arrangements of electrodes to: (1) produce DC (>1 volt) electric fields for electrophoretic induced dynamic movements of the synthetic synzyme structures on the support; (2) produce DC (<1 volt) electric fields for producing short range (double-layer) induced dynamic movements of the synthetic synzyme structures when they are attached very close to or directly to the electrodes; and (3) produce AC electric fields for achieving dielectrophoretic (DEP) induced dynamic movements of the synthetic synzyme structures. Associated electronic equipment (e.g., DC power supplies, frequency generators) allows various combinations of AC and/or DC electric fields to be applied in continuous and/or pulsed and/or oscillated with polarity reversal scenarios in three dimensions (3D) around the synthetic synzyme structures in solution (homogeneous catalysis); as well as for synthetic synzyme structures on supports (heterogeneous catalysis).

Figure 5:
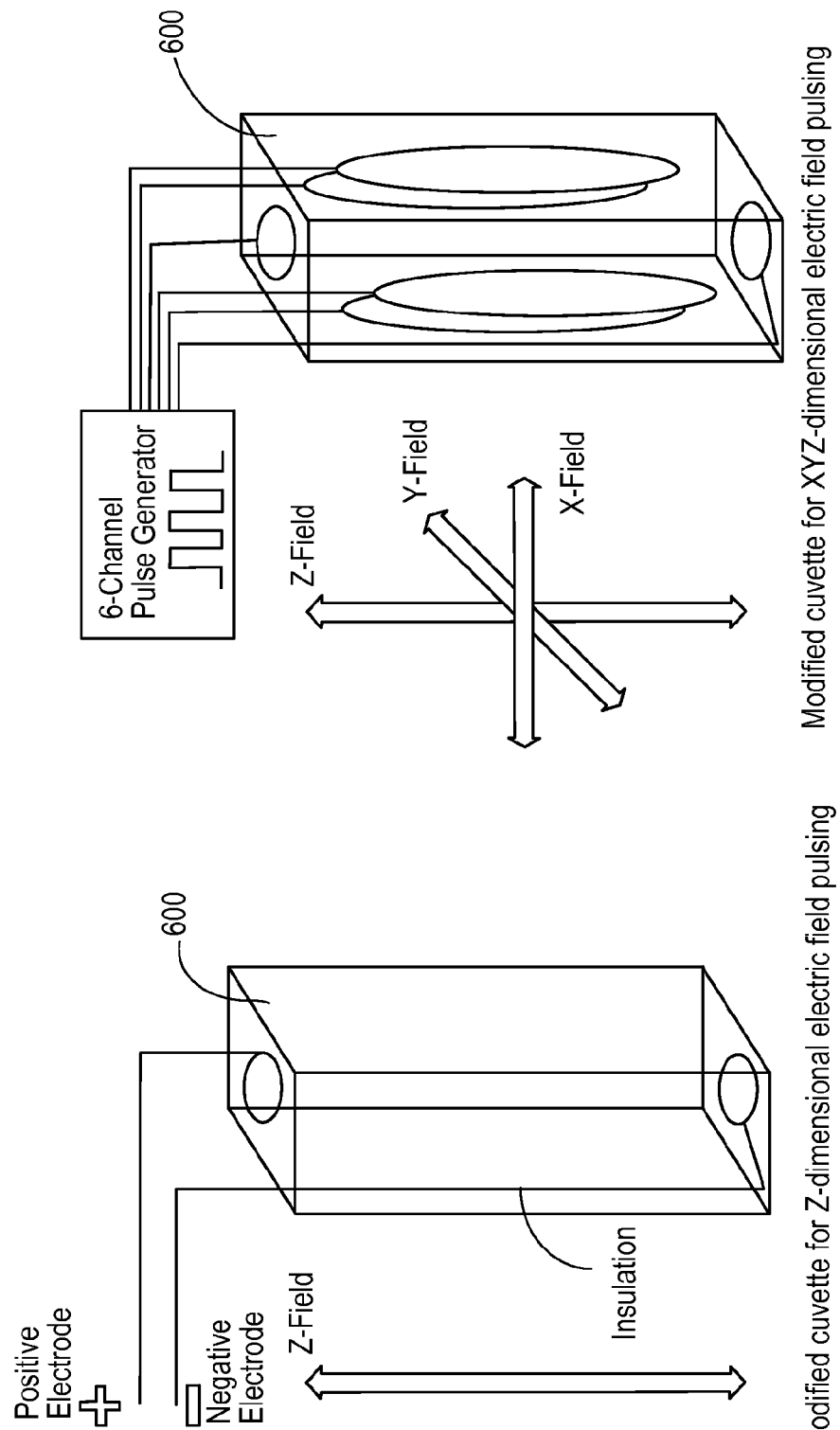
FIG. 5a illustrate an exemplary electric field reaction cell to be used with the synzymes for the application of one dimensional electric field.
FIG. 5b illustrate an exemplary electric field reaction cell to be used with the synzymes for the application of multidimensional electric field.

FIG. 5 show exemplary designs of the electric field reaction well for achieving efficient catalysis using the synzyme structures disclosed herein. FIG. 5a shows a cuvette 600 which contains electrodes on the top (cathode) and bottom (anode) surfaces of the cuvette, creating an electric field in the z-dimension. The negative electrode can be insulated. The cuvette in FIG. 5b contains electrodes on all six surfaces, allowing controllable electric field in all three dimensions (X-Y-Z). Thus multidimensional electric fields can be utilized to finely tune the catalytic dynamic reactions for very high efficiency. In this instance, the modified cuvette 600 as illustrated in FIG. 5b can be connected to a 6-channel pulse generator for the application of DC or AC electric fields.

These devices and systems can be scaled up or down for nano/microscopic applications, intermediate lab-scale applications and for macroscale or industrial, energy (both renewable and non-renewable) and environmental applications; including but not limited to green biomass processing and energy conversions such as cellulose hydrolysis, starch hydrolysis and solar driven water splitting catalysis for hydrogen production. The formats of the devices and systems include but are not limited to various forms of homogeneous (in solution) catalysis, heterogeneous (on support) catalysis which includes fluidized beds as well as various hybrid combinations. Some examples include but are not limited to three dimensional porous support structures with synzymes immobilized within the structures, whose catalytic activity can be enhanced by application of external forces (e.g., electric field), and through which substrates can be flowed into the 3D immobilized synzyme structure and reaction products flowed out of the structure. Such 3D hybrid structures would have the advantages of both homogeneous and heterogeneous catalysis. It is also possible to develop hybrid formats for gas phase catalysis.

In some embodiments, a computer/processor-driven device or apparatus can be configured to design the synthetic polypeptides and other synthetic catalytic structures disclosed herein. For example, a user wishing to design a synzyme having one or more particular characteristics, e.g., a certain rate of turnover, a structure containing one or more particular catalytic groups, enters one or more parameters into the computer/processor-driven device or apparatus, and one or more appropriate synthetic catalytic structures are designed and presented to the user. Such parameters can include, but are not limited to, the particular desired characteristics of the structure. Based on such characteristics, the computer/processor-driven device can utilize, e.g., software using predefined modeling mechanisms or algorithms to determine structures that meet the user's needs. Accordingly, a database or data repository can be utilized to store models, profiles, algorithms, and other data needed to determine the appropriate structure(s). If a user wishes to design synzymes for homogeneous or heterogeneous catalysis applications, the user can specify the type of application in which the synzyme to be designed will be utilized. If the user wishes to design a synthetic synzyme structure with a hand-off mechanism, the user can input such a characteristic as a parameter to be used by the computer/processor-driven device to arrive at an appropriate structure, e.g., one with two histidine groups. Alternatively, a user can enter, e.g., desired catalytic groups, and the computer/processor-driven device can be configured to provide a plurality of possible synzyme structures that have the desired catalytic groups.

It should also be noted that in accordance with another embodiment of the present application, a software application/system/module configured to operate on a computer/processor-driven device or apparatus can be utilized to control the application of external forces to synthetic catalytic structures disclosed herein. For example, such a software application can be used in conjunction with a reaction cell, such as that illustrated in FIGS. 5a and 5b, to program the period of time over which a first directional electric field is applied, the strength of the second directional electric field to be applied, and at what frequency the reverse-polarity electric field is to be oscillated. As also disclosed herein, if a user wishes to apply a continuous or pulsed electric field to a synzyme structure, in which case, the user is given the ability to specify such characteristics of the external force to be applied.

Arrays and Kits

Also provided herein are arrays of synthetic polypeptides. The array can include at least two synthetic polypeptides as described herein. In some embodiments, the array can include at least five synthetic polypeptides. In some embodiments, the array can include at least 15 synthetic polypeptides. In some embodiments, the array of synzymes is attached to a support or substrate, e.g., glass, silicon, or plastic surface, optionally coated with, for example, a porous membrane such as a hydrogel.

Also provided herein are kits of synthetic polypeptides. The kit can include one or more synthetic polypeptides as described herein. The kit can also include instructions for use and other reagents and devices. Instructions for use can include instructions for catalytic applications of the synthetic polypeptides. The instructions for use can be in a paper format or on a CD or DVD. The kit can also include one or more reaction wells, e.g., electric field cuvettes illustrated in FIG. 5a or 5b, to be used with the synzymes. The kit can also include software configured to operate on a computer or processor-driven device or apparatus to control the application of the electric fields to the one or more synthetic polypeptides of the kit.

EXAMPLES

The invention is further described in the following examples, which do not limit the scope of the invention described in the claims.

Example 1

Short synthetic polypeptides that contain the main catalytic groups of the cysteine protease reaction sites were made, and their acetylation and deacylation properties were studied. Polypeptides 1 through 8 consist of nine amino acids, and include various combinations of serine (hydroxyl), cysteine (sulfhydryl/thiol), and histidine (imidazole) residues. The sequences of these synthetic polypeptides and the control polypeptides are shown in Table 2. Polypeptide 1 (SEQ ID NO: 38) consists of a cysteine and a serine but not a histidine residue, which leads to a lack of enzymatic activity and serves as a control polypeptide. Polypeptide 2 (SEQ ID NO: 26) contains a cysteine, a histidine, and an aspartic acid residue to mimic the catalytic triad of a cysteine protease, and uses alanine as the steric spacer between the catalytic residues. Polypeptide 3 (SEQ ID NO: 39) and Polypeptide 4 (SEQ ID NO: 27) are variations of Polypeptide 1 and 2 respectively, with an arginine residue at the N-terminus instead of the glycine residue to provide a charge group. Polypeptide 5 (SEQ ID NO: 29) and Polypeptide 6 (SEQ ID NO: 30) are further variations of Polypeptide 4 (SEQ ID NO: 27), with phenylalanine residues placed between and neighboring the cysteine and histidine residues. Polypeptide 6 (SEQ ID NO: 30) has a lysine at the N-terminus while Polypeptide 5 (SEQ ID NO: 29) has an arginine at the N-terminus Polypeptide 7

(SEQ ID NO: 33) has the cysteine, histidine, and aspartic acid residues in reverse order on the polypeptide chain to investigate the effect of the N-terminal arginine residue on the function of the neighboring aspartic acid residue. Polypeptide 8 (SEQ ID NO: 40) acts as a control for Polypeptide 7 (SEQ ID NO: 33) by replacing the histidine with an asparagine residue which lacks the functionality for acetylation and deacylation. Polypeptide 9 (SEQ ID NO: 37) is a "hand-off" structure that incorporates the similar design of Polypeptide 6, but has two extra histidine residues connected by a proline residue which is thought to bend the polypeptide backbone into a "V" shape structure. Polypeptides 1 through 9 had an overall net negative charge at pH 8.5, allowing them to be oriented in solution by electrophoretic movement toward the positive electrode when a direct current electric field is applied for a short period of time (microsecond to second).

100 μM n-acetyl L-cysteine (Spectrum Chemical) (Control 1), n-acetyl L-histidine (MP Biomedicals) (Control 2), and their combination (Control 3). Each reaction was performed in 0.1× Tris-Borate buffer (pH 8.5) at 25° C. The absorbance of the cleaved p-nitrophenol was measured at 400 nm with Perkin Elmer Lambda 800 UV/Vis Spectrophotometer after a 20 minute reaction time. Second-order rate constants for the acetylation process were determined from the initial rates according to the Equation:

$$k_a = \frac{\text{initial rate} - \text{spontaneous rate}}{[\text{catalyst}][\text{substrate}]}$$

Each polypeptide except Polypeptide 8 (SEQ ID NO: 40) showed a slight increase in acetylation rate constants as

TABLE 2

Acetylation/Deacylation Rate of Exemplary Cysteine-Histidine Synthetic Polypeptides

| Name | Compound/Sequence | Acetylation Rate Constant [1/sec] | Deacylation Rate Constant [mole/sec] | Cys-His Distance [Å] | Charge at pH 8.5 |
|---|---|---|---|---|---|
| Substrate 1 | p-nitrophenol acetate | 92 ± 11 | — | — | — |
| Substrate 2 | acetic anhydride | — | 2.6 ± 1.2 | — | — |
| Control 1 | N-acetyl cysteine | 130 ± 20 | 1.3 ± 0.6 | — | — |
| Control 2 | N-acetyl histidine | 31 ± 8 | 4.0 ± 4.0 | — | — |
| Control 3 | N-acetyl cysteine + N-acetyl histidine | 146 ± 10 | 0.4 ± 0.6 | — | — |
| Polypeptide 1 | Gly-Gly-Ala-Ala-Cys-Ala-Ser-Ala-Asp (SEQ ID NO: 38) | 153 ± 7 | 1.5 ± 1.2 | — | -2.5 |
| Polypeptide 2 | Gly-Gly-Ala-Ala-Cys-Ala-His-Ala-Asp (SEQ ID NO: 26) | 231 ± 16 | 13 ± 11 | 3.6 | -2.5 |
| Polypeptide 3 | Arg-Gly-Ala-Ala-Cys-Ala-Ser-Ala-Asp (SEQ ID NO: 39) | 209 ± 5 | 2.6 ± 1.0 | — | -1.5 |
| Polypeptide 4 | Arg-Gly-Ala-Ala-Cys-Ala-His-Ala-Asp (SEQ ID NO: 27) | 179 ± 7 | 40.2 ± 0.9 | 3.9 | -2 |
| Polypeptide 5 | Arg-Gly-Ala-Phe-Cys-Phe-His-Ala-Asp (SEQ ID NO: 29) | 250 ± 10 | 85 ± 4 | 3.5 | -1.5 |
| Polypeptide 6 | Lys-Gly-Ala-Phe-Cys-Phe-His-Ala-Asp (SEQ ID NO: 30) | 237 ± 8 | 74 ± 8 | 3.7 | -2 |
| Polypeptide 7 | Arg-Asp-Phe-His-Phe-Cys-Ala-Gly-Asp (SEQ ID NO: 33) | 170 ± 20 | 26 ± 3 | 11.0 | -2.5 |
| Polypeptide 8 | Arg-Asp-Phe-Asn-Phe-Cys-Ala-Gly-Asp (SEQ ID NO: 40) | 117 ± 16 | 1.5 ± 1.3 | — | -2.5 |
| Polypeptide 9 | Arg-Gly-Gly-His-Phe-Cys-Gly-Pro-Gly-His-Gly-His-Gly-Asp (SEQ ID NO: 37) | 267 ± 16 | 88 ± 2 | 11.0, 9.5, 15.9 | -1.5 |

Synzyme-substrate reactions were performed and the corresponding acetylation/deacylation rate constants were calculated. Intramolecular distances between the reaction sites Cys-His and Cys-Ser in the polypeptides were studied using molecular modeling.

To test acetylation rate, Polypeptides 1-9 as listed in Table 2, were synthesized (98% purity, Genscript) and diluted in water to 100 μM and reacted with 100 μM of substrate p-nitrophenol acetate (MP Biomedicals) (Substrate 1). The polypeptide reaction rates were studied along with controls:

shown in Table 2. Particularly, Polypeptides 2, 4, 5, 6, and 9 (SEQ ID NO: 26, 27, 29, 30, 37 respectively) showed a statistically significant rate increase compared to the acetyl-cysteine and acetyl-histidine controls.

For Polypeptide 6 (SEQ ID NO: 30), the same acetylation experiments were performed under a variable pH buffer corresponding to S-ion concentrations of 10%, 25%, 50%, 75%, and 90%. The ratio of the rate constant of Polypeptide 6/Control 3 are listed in Table 3. As the pH decreased, the concentration of S-ion decreased and the acetylation becomes more difficult. There was an increase in ratio between the acetylation rate of Polypeptide 6 (SEQ ID NO: 30) and that of Control 3 because the histidine residue on Polypeptide 6 (SEQ ID NO: 30) lowers the pKa of the neighboring cysteine residue, creating more S-ions for acylation. This effect was not seen in Control 3 due to the larger distance between the histidine and cysteine in the homogenous solution.

TABLE 3

Histidine Residue Lowers pKa of
Cysteine Residue of Polypeptide 6

| pH (% S—) | Ratio of Polypeptide 6/ Control 3 Rate Constant |
|---|---|
| pH 7.20 (10% S—) | 2.15 |
| pH 7.74 (25% S—) | 1.76 |
| pH 8.15 (50% S—) | 1.23 |
| pH 8.67 (75% S—) | 1.03 |
| pH 9.13 (90% S—) | 1.00 |

Figure 12:
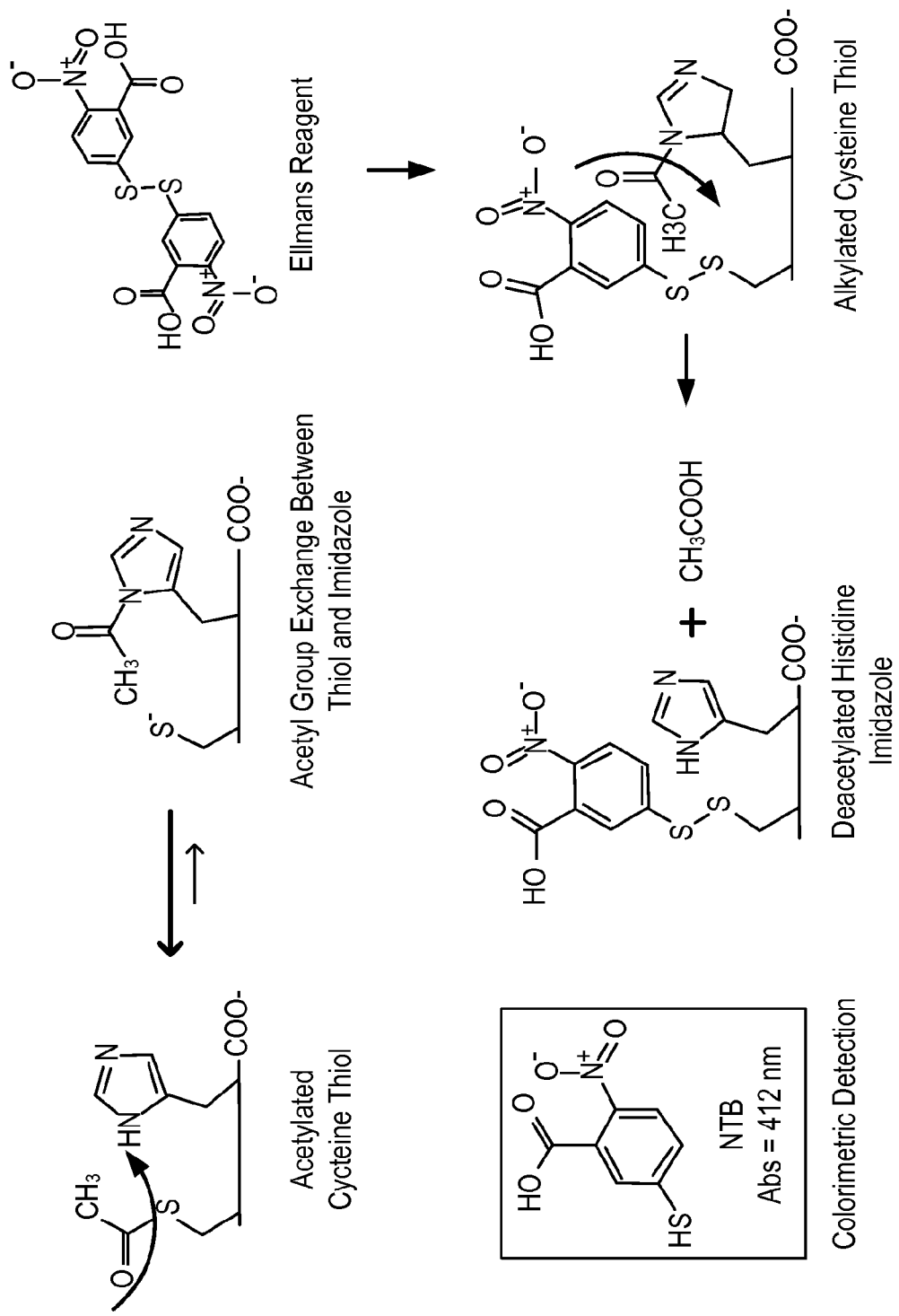
FIG. 12 illustrates the mechanism of the Ellman's reagent trapping experiment.

The deacylation of the synthetic polypeptides were also studied with the same controls using the Ellman's Reagent trapping experiments as shown in FIG. 12. Initially, the polypeptides were acetylated with a 15-fold excess of acetic anhydride (EMG Chemical) (Substrate 2) injected as 10% solution in acetonitrile (Fisher Scientific). The acetylation of the imidazole and the sulfhydryl/thiol group of the polypeptides was observed for 20 minutes at 270 nm and 235 nm, respectively. Subsequently, deacylation was examined by adding Ellman's Reagent (5,5'-dithiobis-(2-nitrobenzoic acid)) (G-Bioscience) at four times the concentration of the polypeptides and the controls. The addition of Ellman's reagent traps any free sulfhydryl/thiol once the cleaved acetyl group leaves the substrate. Deacylation of the acetyl-imidazole was observed by the increase in absorbance of the cleaved Ellman's reagent at 412 nm. A first-order rate constant for the deacylation process was determined with the initial rate according to the Equation:

$$k_a = \frac{\text{initial rate}}{[\text{catalyst}]}$$

Figure 10:
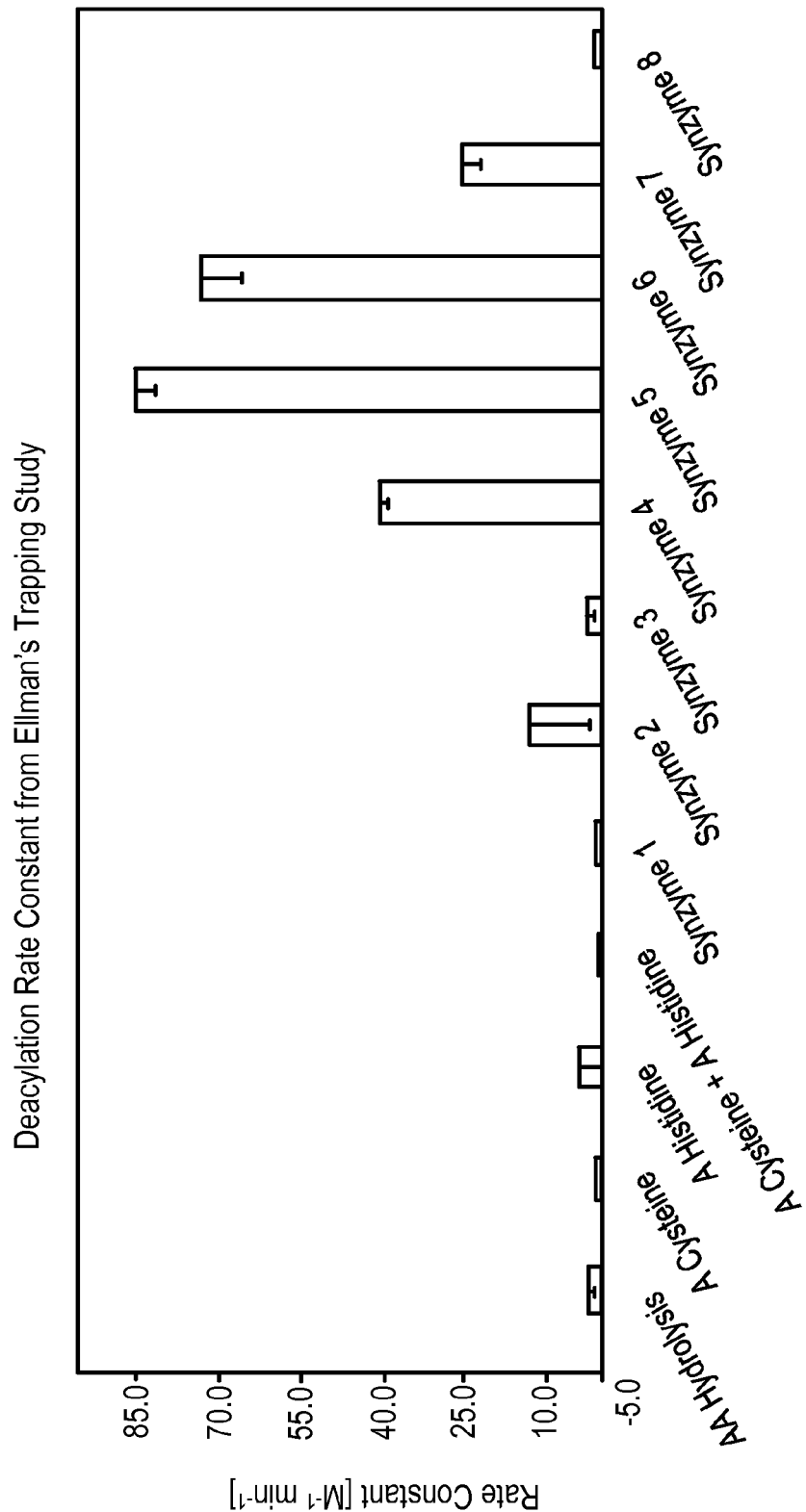
FIG. 10 illustrates exemplary Ellman's reagent trapping deacylation experimental results.

Table 2 presents the first order deacylation rate constants from the Ellman's Reagent trapping study. The controls showed hardly any increase in Ellman's Reagent absorbance, which shows that there is little to no transfer of the acetyl group between the cysteine and histidine molecules in solution. As Table 2 and FIG. 10 show, the trapping effect of the Ellman's reagent was observed with the cysteine-histidine containing Polypeptides 2, 4, 5, 6, 7, 9 (SEQ ID NO: 26, 27, 29, 30, 33, 37, respectively). Polypeptides 1, 3, and 8 (SEQ ID NO: 38, 39, 40 respectively) that lack the histidine catalytic group appeared to be inert. As Table 2 shows, the polypeptides that contained cysteine and histidine in close proximity showed a large increase in Ellman's Reagent reaction, especially Polypeptides 5, 6 and 9 (SEQ ID NO: 29, 30, 37, respectively), which showed an increase in rate constant of over 200 fold. These three polypeptides have a phenylalanine residue in between the cysteine and the histidine residues while the other polypeptides have an alanine residue in between the cysteine and the histidine residues. Polypeptide 5 (SEQ ID NO: 29) with an arginine residue at the N-terminal position exhibited enhanced deacylation rate when compared to Polypeptide 6 (SEQ ID NO: 30) that has a lysine residue at the N-terminus and otherwise identical amino acid sequence as Polypeptide 5.

Table 2 also lists the distance between the cysteine sulfhydryl/thiol group and the histidine imidazole group measured for Polypeptides 2, 4, 5, 6, and 7 (SEQ ID NO: 26, 27, 29, 30, 33, respectively) by modeling each polypeptide in Accelrys Discovery Studio 3.5 with Dreding-like forcefield applied to minimize the intermolecular energy. The three values listed for Polypeptide 9 (SEQ ID NO: 37) represent the distance between the cysteine sulfhydryl/thiol group and the imidazole group of the three histidine residues in the order appearing on the sequence. Polypeptide 5 (SEQ ID NO: 29) had the shortest sulfhydryl/thiol-imidazole distance of 3.5 Å and the polypeptide itself had the second highest acetylation and deacylation rate constants. There is a general trend that shorter sulfhydryl/thiol-imidazole distances achieve faster reaction rates for both acetylation and deacylation.

Despite having larger sulfhydryl/thiol-imidazole distances, slightly higher acetylation and deacylation rate constants were observed with Polypeptide 9 (SEQ ID NO: 37) which includes a "hand-off" structure containing three histidine residues and a proline residue. Proline creates a tight turn in the polypeptide chain and brings the second and third histidine into close proximity with the first histidine and the cysteine residue. The second and third histidine residues were positioned in a way that compete with the sulfhydryl/thiol group for binding to the acyl group on the acyl-imidazole intermediate and move the acyl group further away from the sulfhydryl/thiol group to reduce back-attack from the sulfhydryl/thiol group. Such competition is likely the reason for Polypeptide 9 (SEQ ID NO: 37) to show enhanced deacylation rates.

These results demonstrate that short synthetic polypeptides can be used to mimic some of the precise conformational changes necessary for catalytic activities seen in real enzymes. Slight structural changes in these synthetic polypeptides have a significant impact on the deacylation rate and turnover of the synzymes. Thus strategic positioning of the main reaction sites is the key to design synzymes with superior catalytic activities.

Example 2

Figure 11:
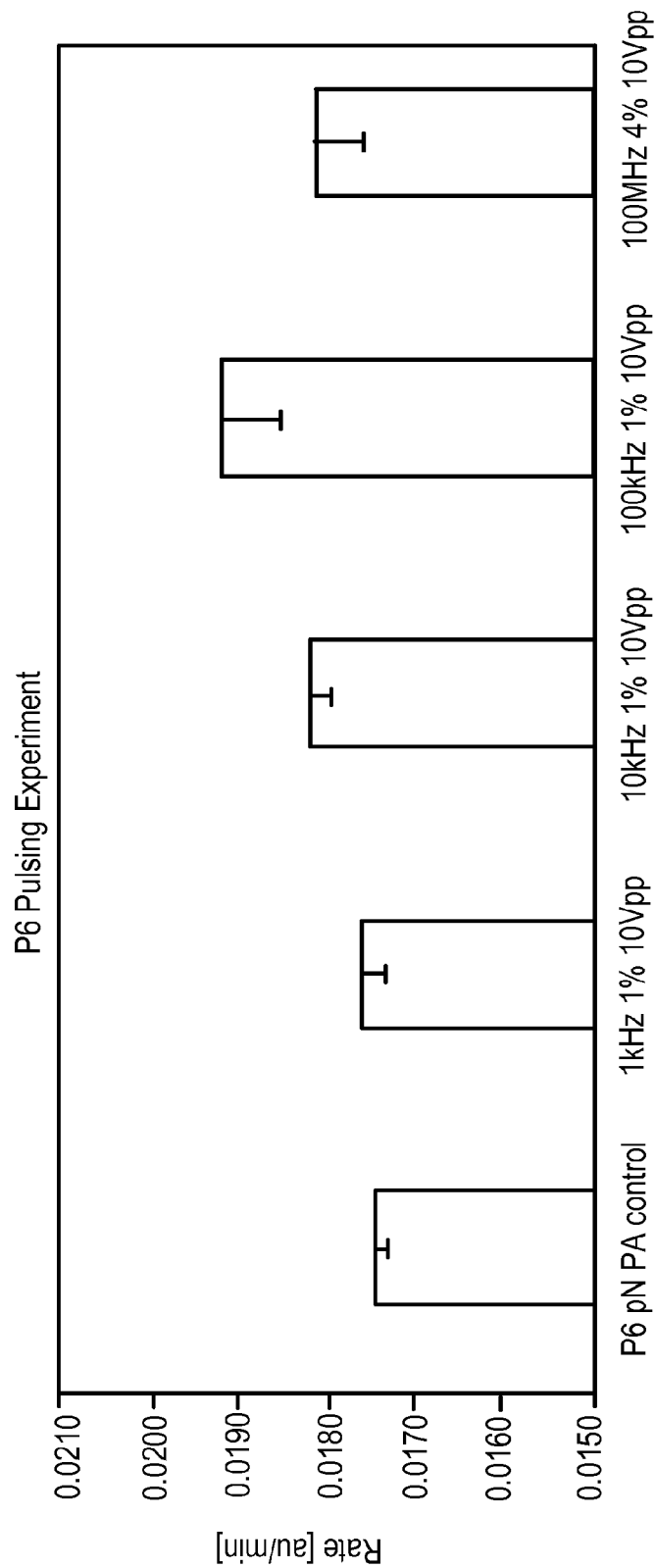
FIG. 11 illustrates exemplary effects of a DC electric field on the acetylation and deacylation of a polypeptide synzyme.

The activity of Polypeptide 6 (SEQ ID NO: 30) was further evaluated in the presence of the application of an electric field. The Ellman's trapping experiment was performed as described in Example 1. The electric field was applied after the addition of the Ellman's reagent for 30 minutes. FIG. 11 shows the acetylation/deacetylation rate of Polypeptide 6 (SEQ ID NO: 30) when pulsed at different electric frequencies. At 100 kHz, 1% duty cycle, 10 volts pk-pk, Polypeptide 6 (SEQ ID NO: 30) clearly shows an increase in the deacylation rate, indicating back-attack has been reduced. These results demonstrate that an electric field can positively affect the catalytic properties of the synzymes.

The ability to develop synthetic catalysts which operate under mild conditions (e.g., mild temperature and/or pressure) would have a large impact on many biotechnology and biomedical areas, including powering in vivo diagnostic and therapeutic devices. As importantly, synzymes would have major impact in the chemical, renewable energy, food processing, waste processing and environmental related industries. Exemplary uses include, but are not limited to, synthetic catalysis for production of hydrogen, ethanol production, cellulose hydrolysis, high fructose corn syrup production, catalyst for fuel cells and for "cold fusion" energy producing devices.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations. As used herein, the term "module" can describe a given unit of functionality that can be performed in accordance with one or more embodiments of the present invention. As used herein, a "module" might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality. Where components or modules of the invention are implemented in whole or in part using software, in one embodiment, these software elements can be implemented to operate with a computing or processing module capable of carrying out the functionality described with respect thereto.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A synthetic polypeptide comprising an amino acid sequence selected from the group consisting of:

```
                                        (SEQ ID NO: 22)
    Gly-Ala-Phe-Cys-Phe-His-Ala-Asp;

(SEQ ID NO: 23)
    Gly-Ala-Phe-Ser-Phe-His-Ala-Asp;

(SEQ ID NO: 24)
    Asp-Phe-His-Phe-Cys-Ala-Gly-Asp;

(SEQ ID NO: 25)
    Asp-Phe-His-Phe-Ser-Ala-Gly-Asp;

(SEQ ID NO: 26)
    Gly-Gly-Ala-Ala-Cys-Ala-His-Ala-Asp;

(SEQ ID NO: 27)
    Arg-Gly-Ala-Ala-Cys-Ala-His-Ala-Asp;

(SEQ ID NO: 28)
    Arg-Gly-Ala-Ala-Ser-Ala-His-Ala-Asp;

(SEQ ID NO: 29)
    Arg-Gly-Ala-Phe-Cys-Phe-His-Ala-Asp;

(SEQ ID NO: 30)
    Lys-Gly-Ala-Phe-Cys-Phe-His-Ala-Asp;

(SEQ ID NO: 31)
    Arg-Gly-Ala-Phe-Ser-Phe-His-Ala-Asp;

(SEQ ID NO: 32)
    Lys-Gly-Ala-Phe-Ser-Phe-His-Ala-Asp;

(SEQ ID NO: 33)
    Arg-Asp-Phe-His-Phe-Cys-Ala-Gly-Asp;

(SEQ ID NO: 34)
    Arg-Asp-Phe-His-Phe-Ser-Ala-Gly-Asp;

(SEQ ID NO: 36)
    Arg-Gly-His-Gly-Gly-Pro-Gly-Gly-His-
    Gly-Cys-Gly-Asp;
and
                                        (SEQ ID NO: 37)
    Arg-Gly-Gly-His-Phe-Cys-Gly-Pro-Gly-
    His-Gly-His-Gly-Asp,
``` and wherein the synthetic polypeptide is from 6 to 30 amino acids total in length.

2. The synthetic polypeptide of claim 1, wherein the synthetic polypeptide comprises an amino acid sequence selected from the group consisting of:

```
                                                (SEQ ID NO: 26)
Gly-Gly-Ala-Ala-Cys-Ala-His-Ala-Asp;

(SEQ ID NO: 27)
Arg-Gly-Ala-Ala-Cys-Ala-His-Ala-Asp;

(SEQ ID NO: 28)
Arg-Gly-Ala-Ala-Ser-Ala-His-Ala-Asp;

(SEQ ID NO: 29)
Arg-Gly-Ala-Phe-Cys-Phe-His-Ala-Asp;

(SEQ ID NO: 30)
Lys-Gly-Ala-Phe-Cys-Phe-His-Ala-Asp;

(SEQ ID NO: 31)
Arg-Gly-Ala-Phe-Ser-Phe-His-Ala-Asp;

(SEQ ID NO: 32)
Lys-Gly-Ala-Phe-Ser-Phe-His-Ala-Asp;

(SEQ ID NO: 33)
Arg-Asp-Phe-His-Phe-Cys-Ala-Gly-Asp;
and (SEQ ID NO: 34)
Arg-Asp-Phe-His-Phe-Ser-Ala-Gly-Asp,
``` and
wherein the synthetic polypeptide is from 9 to 15 amino acids total in length.

3. The synthetic polypeptide of claim 1, wherein the synthetic polypeptide comprises the amino acid sequence Arg-Gly-His-Gly-Gly-Pro-Gly-Gly-His-Gly-Cys-Gly-Asp (SEQ ID NO: 36), and wherein the synthetic polypeptide is from 13 to 30 amino acids total in length.

4. The synthetic polypeptide of claim 1, wherein the synthetic polypeptide comprises a negatively charged C-terminal residue selected from the group consisting of aspartic acid, glutamic acid, methyl aspartic acid, methyl glutamic acid, 2-aminoadipic acid, 2-aminoheptanedioic acid, and iminodiacetic acid.

5. The synthetic polypeptide of claim 1, wherein the synthetic polypeptide comprises an N-terminal residue selected from the group consisting of glycine, lysine, arginine, citrulline, ornithine, and 2-amino-3-guanidinopropionic acid.

6. The synthetic polypeptide of claim 1, wherein the N-terminus of the synthetic polypeptide is protected and uncharged.

7. The synthetic polypeptide of claim 6, wherein the N-terminus of the synthetic polypeptide is protected by a group selected from an acetyl, tert-butyloxycarbonyl, 9-fluorenylmethyloxycarbonyl, benzoyloxycarbonyl, carbobenzyloxy, p-methoxybenzyl, p-methoxybenzyl carbonyl, benzoyl, benzyl, carbamate, p-methoxyphenyl, 3,4-dimethoxybenzyl, and tosyl group.

8. The synthetic polypeptide of claim 1, wherein the C-terminus of the synthetic polypeptide is protected and uncharged.

9. The synthetic polypeptide of claim 8, wherein the C-terminus of the synthetic polypeptide is protected by a group selected from a methyl, ethyl, benzyl, tert-butyl, silyl, and phenyl group.

10. The synthetic polypeptide of claim 1, wherein the synthetic polypeptide comprises the amino acid sequence Arg-Gly-Gly-His-Phe-Cys-Gly-Pro-Gly-His-Gly-His-Gly-Asp (SEQ ID NO: 37), and wherein the synthetic polypeptide is from 14 to 30 amino acids total in length.

11. A synthetic polypeptide of claim 1, wherein the synthetic polypeptide is immobilized onto a solid surface.

12. The synthetic polypeptide of claim 11, wherein the synthetic polypeptide is immobilized onto a solid surface through a charged group of the synthetic polypeptide, and wherein the charged group is selected from the group consisting of an α-amino group, an α-carboxyl group, an ε-amino group, and a sulfhydryl/thiol group.

13. The synthetic polypeptide of claim 12, wherein the charged group is located on a terminal residue of the synthetic polypeptide.

14. The synthetic polypeptide of claim 12, wherein the charged group is located on a residue within one to five amino acids from a terminus of the synthetic polypeptide.

15. The synthetic polypeptide of claim 12, wherein the charged group is located on a linker conjugated to the synthetic polypeptide.

16. An array of synthetic polypeptides comprising at least two synthetic polypeptides, wherein each synthetic polypeptide is from 9 to 15 amino acids total in length and comprises an amino acid sequence selected from the group consisting of:

```
                                                (SEQ ID NO: 22)
Gly-Ala-Phe-Cys-Phe-His-Ala-Asp;

(SEQ ID NO: 23)
Gly-Ala-Phe-Ser-Phe-His-Ala-Asp;

(SEQ ID NO: 24)
Asp-Phe-His-Phe-Cys-Ala-Gly-Asp;

(SEQ ID NO: 25)
Asp-Phe-His-Phe-Ser-Ala-Gly-Asp;

(SEQ ID NO: 26)
Gly-Gly-Ala-Ala-Cys-Ala-His-Ala-Asp;

(SEQ ID NO: 27)
Arg-Gly-Ala-Ala-Cys-Ala-His-Ala-Asp;

(SEQ ID NO: 28)
Arg-Gly-Ala-Ala-Ser-Ala-His-Ala-Asp;

(SEQ ID NO: 29)
Arg-Gly-Ala-Phe-Cys-Phe-His-Ala-Asp;

(SEQ ID NO: 30)
Lys-Gly-Ala-Phe-Cys-Phe-His-Ala-Asp;

(SEQ ID NO: 31)
Arg-Gly-Ala-Phe-Ser-Phe-His-Ala-Asp;

(SEQ ID NO: 32)
Lys-Gly-Ala-Phe-Ser-Phe-His-Ala-Asp;

(SEQ ID NO: 33)
Arg-Asp-Phe-His-Phe-Cys-Ala-Gly-Asp;

(SEQ ID NO: 34)
Arg-Asp-Phe-His-Phe-Ser-Ala-Gly-Asp;

(SEQ ID NO: 36)
Arg-Gly-His-Gly-Gly-Pro-Gly-Gly-His-Gly-Cys-Gly-
Asp;
and (SEQ ID NO: 37)
Arg-Gly-Gly-His-Phe-Cys-Gly-Pro-Gly-His-Gly-His-
Gly-Asp.
```

17. The array of the synthetic polypeptides of claim 16, wherein the array of synthetic polypeptides comprises at least five synthetic polypeptides.

18. The array of the synthetic polypeptides of claim 16, wherein the array of synthetic polypeptides comprises at least 15 synthetic polypeptides.

19. The array of the synthetic polypeptides of claim 16, wherein the synthetic polypeptides are immobilized on a support or substrate.

20. A kit comprising one or more synthetic polypeptides of claim 1.

21. The kit of claim 20, wherein the kit further comprises one or more reaction wells.

22. The kit of claim 21, wherein the one or more reaction wells are electric field cuvettes.

23. The kit of claim 20, wherein the kit further comprises software configured to control application of electric fields to the one or more synthetic polypeptides of the kit.

24. A method of hydrolyzing an amide or ester bond in a substrate comprising: contacting an amide or ester bond containing substrate with one or more synthetic polypeptide of claim 1.

25. The method of claim 24, wherein the amide or ester bond containing substrate is a peptide, protein, fatty acid, or glycerol ester.

26. The method of claim 24, wherein step of contacting the amide or ester bond containing substrate is performed under conditions where a cysteine or cysteine analog, or a serine or serine analog of the synthetic polypeptide is nucleophilic,
wherein the cysteine analog is selected from the group consisting of homocysteine and penicillamine; and
wherein the serine analog is selected from the group consisting of methylserine, threonine, 2-amino-3-hydroxy-4-methylpentanoic acid, 3-amino-2-hydroxy-5-methylhexanoic acid, 4-amino-3-hydroxy-6-methylheptanoic acid, and 2-amino-3-hydroxy-3-methylbutanoic acid.

27. The method of claim 24, wherein the step of contacting the amide or ester bond containing substrate is performed under conditions that allow formation of an acyl-sulfhydryl/thiol intermediate with the cysteine or cysteine analog, or an acyl-hydroxyl intermediate with the serine or serine analog, of the synthetic polypeptide.

28. The method of claim 24, wherein the step of contacting the amide or ester bond containing substrate is performed under conditions that allow formation of an acyl-imidazole intermediate.

29. The method of claim 24, further comprising applying an external electric field.

30. The method of claim 29, wherein the external electrical field is applied in either one direction or in multiple directions.

31. The method of claim 29, wherein the step of applying an external electric field comprises:
  (i) applying a first directional electric field for less than one second to orient the synthetic polypeptide;
  (ii) applying a second stronger directional electric field to facilitate formation of an acyl-imidazole intermediate; and
  (iii) applying a third oscillating electric field to reduce the physical proximity of the acyl-imidazole intermediate and a nucleophilic sulfhydryl/thiol or hydroxyl group of the synthetic polypeptide.

* * * * *